(12) United States Patent
Chong

(10) Patent No.: US 8,690,328 B1
(45) Date of Patent: Apr. 8, 2014

(54) METHODS AND DEVICES FOR OPHTHALMIC OPTICAL TOMOGRAPHIC IMAGE DISPLAY

(71) Applicant: Santec Corporation, Aichi (JP)

(72) Inventor: Changho Chong, Komaki (JP)

(73) Assignee: Santec Corporation, Komaki, Aichi (JP)

( * ) Notice: Subject to any disclaimer, the term of this patent is extended or adjusted under 35 U.S.C. 154(b) by 0 days.

(21) Appl. No.: 13/892,997

(22) Filed: May 13, 2013

(30) Foreign Application Priority Data

Jan. 30, 2013 (JP) ................. 2013-015264

(51) Int. Cl.
*A61B 3/10* (2006.01)
*A61B 3/14* (2006.01)
*A61B 3/12* (2006.01)

(52) U.S. Cl.
CPC *A61B 3/14* (2013.01); *A61B 3/1225* (2013.01)
USPC ............. 351/206; 351/205; 351/221

(58) Field of Classification Search
USPC .......... 351/205, 206, 221; 356/450, 477, 479; 600/407, 425
See application file for complete search history.

(56) References Cited

U.S. PATENT DOCUMENTS

| | | | |
|---|---|---|---|
| 4,466,699 A | 8/1984 | Droessler et al. | |
| 5,022,745 A | 6/1991 | Zayhowski et al. | |
| 5,319,668 A | 6/1994 | Luecke | |
| 5,430,574 A | 7/1995 | Tehrani | |
| 5,561,523 A | 10/1996 | Blomberg et al. | |
| 6,111,645 A | 8/2000 | Tearney et al. | |
| 6,134,003 A | 10/2000 | Tearney et al. | |
| 6,275,718 B1* | 8/2001 | Lempert ................. | 600/407 |
| 6,282,011 B1 | 8/2001 | Tearney et al. | |
| 6,373,632 B1 | 4/2002 | Flanders | |
| 6,421,164 B2 | 7/2002 | Tearney et al. | |
| 6,485,413 B1 | 11/2002 | Boppart et al. | |
| 6,501,551 B1 | 12/2002 | Tearney et al. | |
| 6,564,087 B1 | 5/2003 | Pitris et al. | |
| 7,099,358 B1 | 8/2006 | Chong | |

(Continued)

FOREIGN PATENT DOCUMENTS

| | | |
|---|---|---|
| JP | 2008-188047 | 8/2008 |
| JP | 2010-172538 | 8/2010 |

OTHER PUBLICATIONS

Changho Chong, et al. "Large Coherence Length Swept Source for Axial Length Measurement of the Eye." Applied Optics 48:10 (2009): D144-150.

(Continued)

*Primary Examiner* — Mahidere Sahle
(74) *Attorney, Agent, or Firm* — Foley & Lardner LLP

(57) ABSTRACT

Embodiments of the present disclosure includes optical tomographic methods and systems for acquiring information based on an image precisely in a short time. In one example, an optical tomographic imaging device may irradiate light on an eye which is the object to be measured via an interferometer 13 using a wavelength scanning-type laser light source 11, and acquire a cross-sectional image. The optical tomographic imaging device may include an object lens 23 at the focus position of the two-axis tilt mirror 22. It may deflect light in the x-axis and y-axis direction using the two-axis tilt mirror 22 and obtain a three-dimensional cross-sectional image without having distortion in the optical axis direction.

26 Claims, 28 Drawing Sheets

(56) References Cited

U.S. PATENT DOCUMENTS

| | | |
|---|---|---|
| 7,323,680 B2 | 1/2008 | Chong |
| 7,352,783 B2 | 4/2008 | Chong |
| 7,382,809 B2 | 6/2008 | Chong et al. |
| 7,388,891 B2 | 6/2008 | Uehara et al. |
| 7,414,779 B2 | 8/2008 | Huber et al. |
| 7,489,713 B2 | 2/2009 | Chong et al. |
| 7,701,588 B2 | 4/2010 | Chong |
| 7,835,010 B2 | 11/2010 | Morosawa et al. |
| 7,884,945 B2 | 2/2011 | Srinivasan et al. |
| 8,315,282 B2 | 11/2012 | Huber et al. |
| 8,405,834 B2 | 3/2013 | Srinivasan et al. |
| 2005/0201432 A1 | 9/2005 | Uehara et al. |
| 2009/0103050 A1* | 4/2009 | Michaels et al. ............... 351/208 |
| 2010/0157308 A1* | 6/2010 | Xie ................................ 356/477 |
| 2011/0255054 A1 | 10/2011 | Hacker et al. |
| 2012/0136259 A1* | 5/2012 | Milner et al. .................. 600/478 |

OTHER PUBLICATIONS

F. Lexer et al., "Wavelength-tuning interferometry of intraocular distances," Applied Optics, vol. 36, No. 25, pp. 6548-6553 (Sep. 1, 1997).

P. Tayebati et al., "Microelectromechanical tunable filter with stable half symmetric cavity," Electronics Letters, vol. 34, No. 20, pp. 1967-1968 (Oct. 1, 1998).

Sergio Ortiz, et al. "Corneal Topography From Spectral Optical Coherence Tomography (SOCT)." Biomedical Optics Express 2:12, (2011):3232-3247.

* cited by examiner

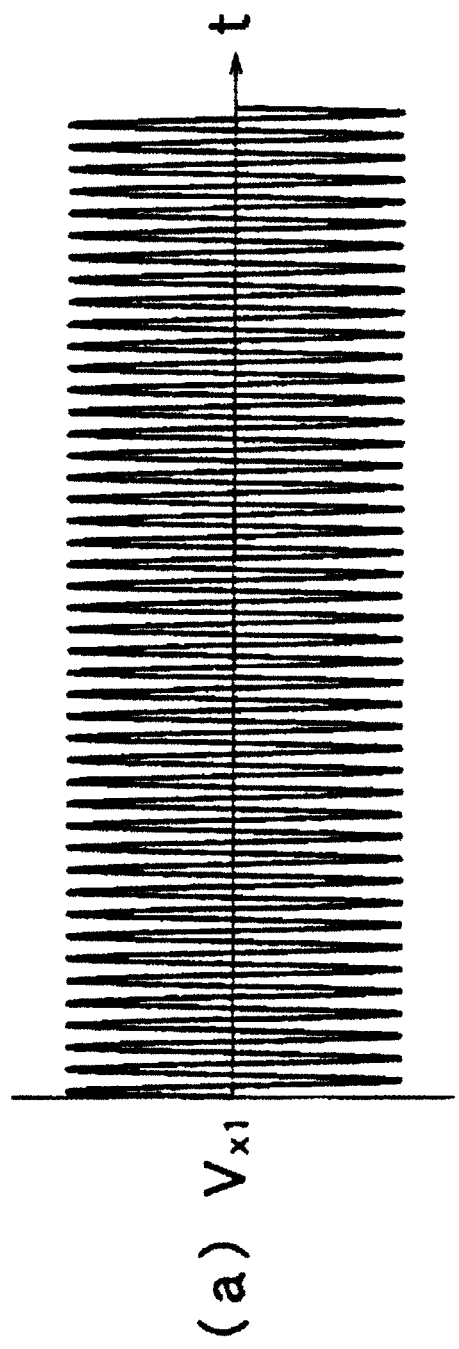
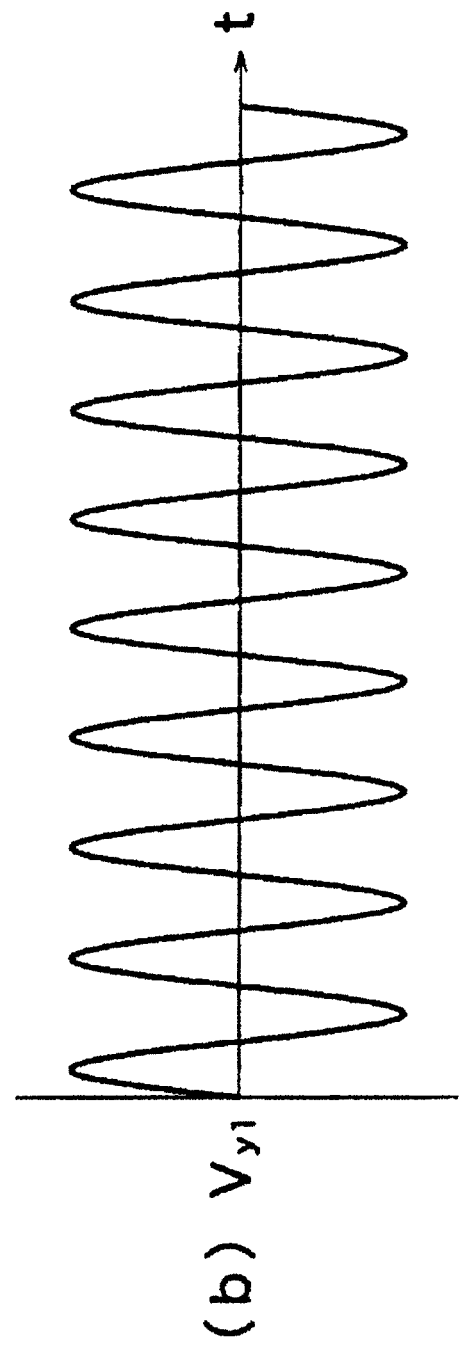
FIG. 3

(a)
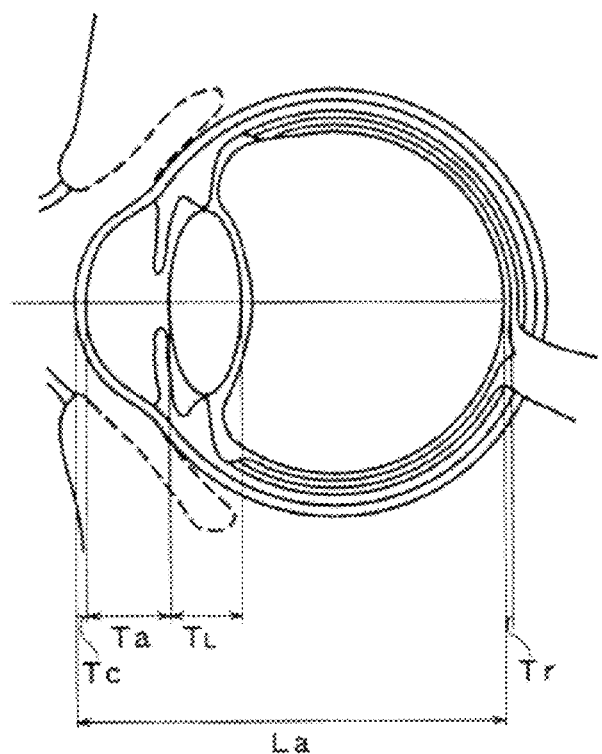
(b)
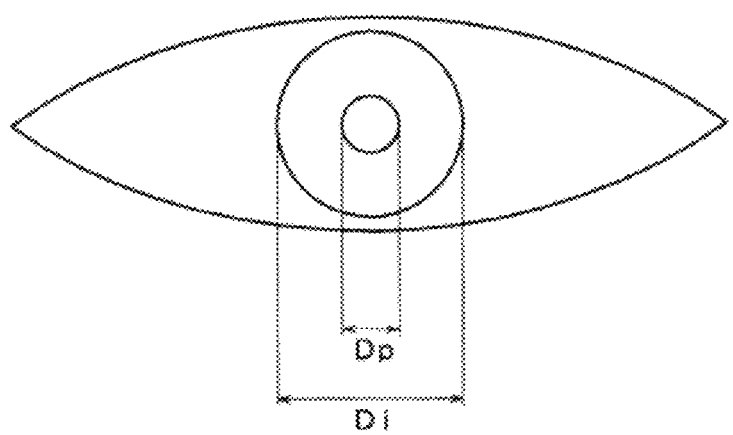
FIG. 11

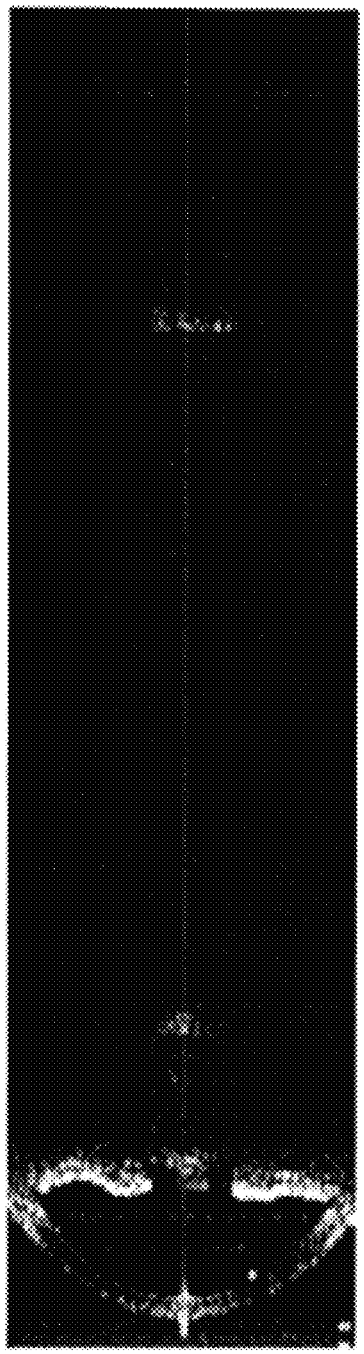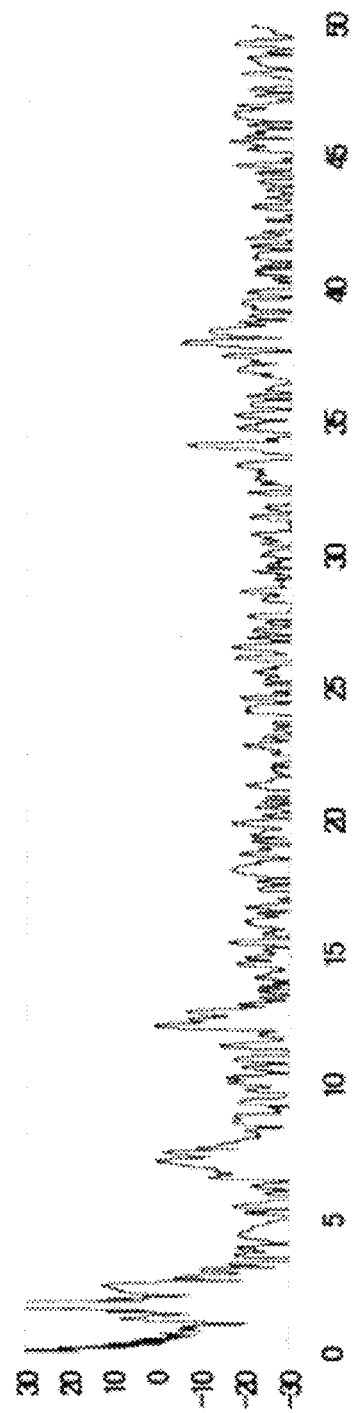
Reflective level
(a) (b)
FIG. 24

(a)
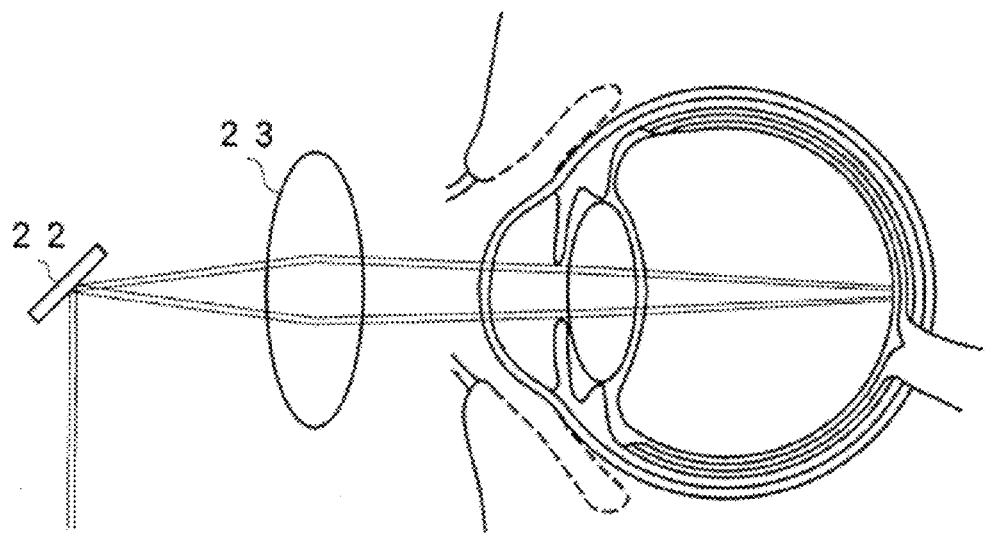
(b)
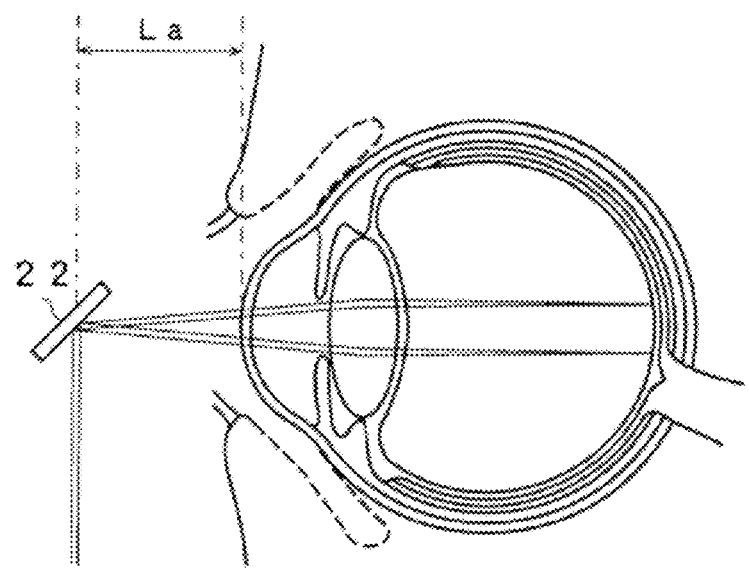
FIG. 26

(a) 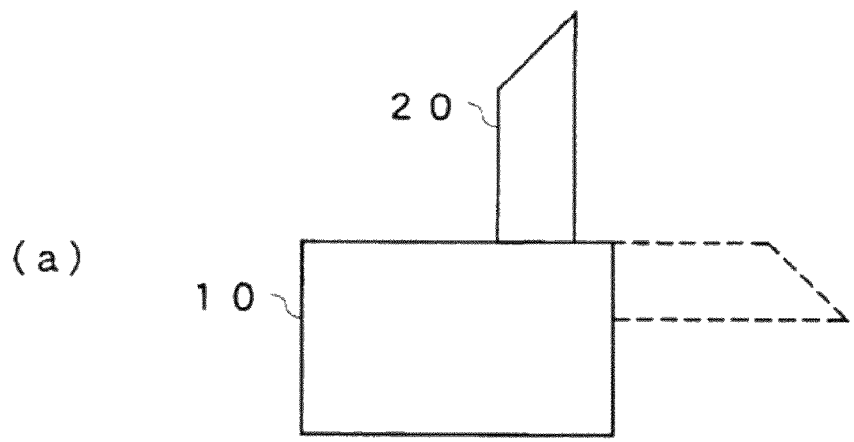
(b) 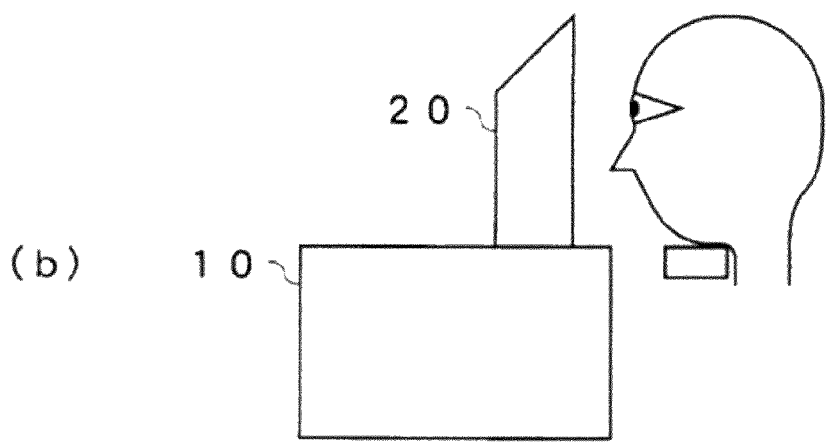
(c) 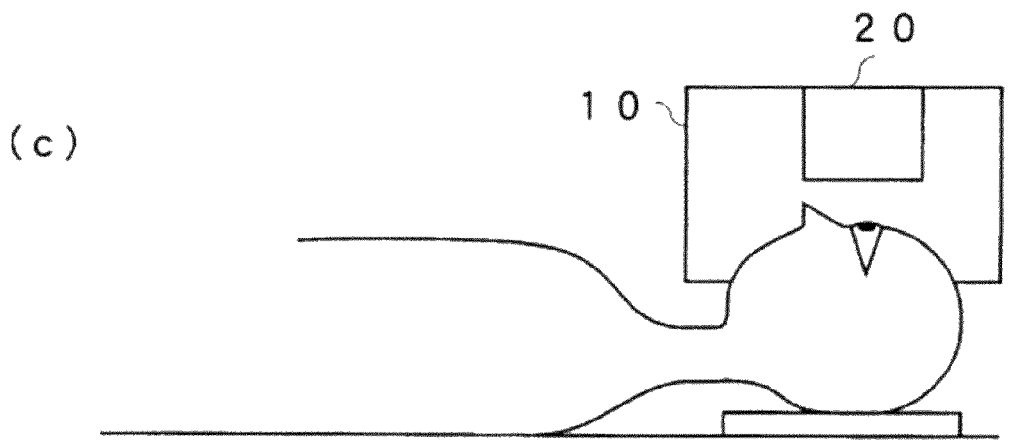
FIG. 28

METHODS AND DEVICES FOR OPHTHALMIC OPTICAL TOMOGRAPHIC IMAGE DISPLAY

CROSS-REFERENCE TO RELATED PATENT APPLICATION

This applications claims the benefit, under 35 U.S.C. §119 (a), of Japanese Patent Application No. 2013-015264, filed on Jan. 30, 2013, and entitled "Optical Tomographic Image Display Device," which is incorporated herein by reference in its entirety.

BACKGROUND

There are a large number of patients with cataracts, and when the condition worsens, an operation to insert an intraocular lens (IOL) is needed. In the operation to insert an intraocular lens for cataracts, it is necessary to measure at least the ocular axial length and the cornea curvature radius of the patient. At that time, if the measurement is not taken accurately, there will be a difference in vision between the two eyes after an operation. Preferably, the difference in vision between the two eyes should be as small as possible, and it is necessary to leave it in the range of at least ±1D. Therefore, there is a need to improve the precision of these measurements as much as possible.

Conventionally, to measure the ocular axial length and a curvature radius, there is an ultrasound measurement method as shown in Japanese Patent Laid-Open No. 2010-172538, and an optical measurement method as shown in Japanese Patent Laid-Open No. 2008-188047. As well as the need for anesthesia in the ultrasound method, this technique is very hard on the patient physically, and it requires a great deal of skill on the part of the doctor to perform the operation.

The conventional optical ocular axial length measurement device put to practical use uses a time-domain interference method. In the time-domain device using the ocular axial length measurement, the infrared light beam in the 780-840 nm band is irradiated perpendicularly against the eyeball via an interferometer, the light path difference of the reflected light from the cornea and the reflected light from the retina are detected by the movement of each of the reference mirrors, and the ocular axial length is found by calculating the difference. According to this method, the value of the corneal thickness or the lens thickness, or other thickness can also be theoretically detected.

However, there were problems in this measurement device in that it was highly possible that an error would be generated based on the error signal due to the method for moving the reference mirror of the interferometer mechanically, and due to measuring the ocular axial length from a one-dimensional signal. Further, there was the problem that it was necessary to take, for example, around five measurements and then use the average reading, and each measurement took a long time from around 30 seconds to a minute. In addition, there was the problem that if the measurement took a long time, the patients did not remain still, the measurement conditions were not uniform, precise measurement could not be taken, and more time was needed for a diagnosis.

Furthermore, in the case of severe cataract patients, there are times where the ocular axial length cannot be measured without arriving at the retina, since the infrared measurement light is scattered in the clouded crystalline lens. In such cases, the optical measurement of Japanese Patent Laid-Open No. 2008-188047 is not dependable.

On the other hand, Changho Chong et al., "Large Coherence Length Swept Source for Axial Length Measurement of the Eye," Applied Optics 48:10 (2009): D145-150 suggests a method to measure the ocular axial length by a two-dimensional optical coherence tomography (OCT) image using the wavelength scanning-type-light source (hereinafter referred to as swept-source OCT (SS-OCT)) in the 1 μm band. Since the wavelength in the 1 μm band is a wavelength longer than 800 nm band, and the tolerance value of the optical power that can go into the eyes is high, the light easily arrives at the retina, and since the sensitivity by the SS-OCT method is 20 dB or more higher than that by the time-domain method, it can be expected that the measurement success rate improves. In addition, the scan rate is faster from several kHz to several tens of kHz, therefore a precise measurement can be taken since there is little influence from the blur caused by the movement of the eyes of the patient.

To calculate the power of the intraocular lens, it is necessary to calculate the curvature radius of the cornea as well as the parameter of length, such as the ocular axial length or the anterior chamber thickness. The measurement of curvature radius of the cornea is called keratometry (sic: corneal warpage). Illumination light is mainly irradiated on the corneal surface and the curvature in the range of a two or three mm diameter is generally calculated from the top of the cornea based on the position of the calescence point of the source of light that moved to the surface.

SUMMARY

Embodiments of the present invention relate to an optical tomographic image display device capable of displaying the object to be measured as a cross-sectional image without making a contact or invasion, and more specifically to an ophthalmic optical tomographic image display device.

In a normal ocular-axial-length measurement device, as described above, only a parameter of length, such as the ocular axial length, can be measured. To measure the curvature radius of the cornea, it was necessary to have a CCD sensor that caught a plurality of illumination lights or ring illumination and reflected it on the cornea surface as an image, or a mechanism or software to separately calculate the cornea curvature radius from the diameter or distortion factor of the image in all directions.

Contrary to this, if a two-dimensional tomography of the eyes could be obtained using the SS-OCT method, as shown in Changho Chong et al., "Large Coherence Length Swept Source for Axial Length Measurement of the Eye," Applied Optics 48:10 (2009): D145-150, the curvature could be read from the tomographic image information of this cornea. However, in the case of astigmatism, it is necessary to divide the 360° perimeter into four or more divisions to find the curvature of each cornea curved surface, since the curvature radiuses of the cornea are different depending on the direction.

However, when a general two-axis galvanometer mirror or the like is used for the probe part to scan the light in a two-axis (x-axis, y-axis) direction, the beam scan does not scan completely parallel in the x and y directions since a different mirror is used for each axis. Therefore, as shown in Sergie Ortiz et al., "Corneal Topography From Spectral Optical Coherence Tomography (SOCT)," Biomedical Optics Express 2:12, (2011):3232-3247, it is necessary to calibrate using the grid patterns at each optical axis direction position (depth) where the x, y focal plane is distorted in the optical axis direction and correct the image that was acquired three-dimensionally. When distortion occurs in the focal plane in this manner, there are problems that require very complicated calibration and revision calculations to revise the surface shape.

The present invention was devised in view of such conventional problems and the object is to be able to precisely measure two-dimensional image data with the SS-OCT method in a short time, and acquire necessary information based on this image.

In order to solve the above described problems, the ophthalmic optical tomographic image display device according to the present invention comprises: a scanning-type source of light to periodically scan an oscillation wavelength of the light; an interferometer configured such that the light from the scanning-type light source is diverged to the reference light and irradiation light to the object, and the reflected light from the object and interference light with the reference light are generated; a probe that is provided at the object position of the interferometer to consecutively scan the irradiation position of the light to the object; a light-receiving element subjected to light by the interference light to be obtained from the interferometer to acquire a beat signal; and an image signal processing unit to generate the tomographic image of the object to be measured by Fourier transform of the light-receiving signal obtained from the light-receiving element; wherein the probe comprises: an object lens to condense the parallel beam, and a two-axis tilt mirror positioned at the focus position of the object lens to scan a parallel beam in the x-axis direction that is perpendicular to the eyes and in the perpendicular y-axis direction parallel to this.

The wavelength scanning-type light source may be configured to scan a wavelength at a scanning speed of 1 kHz or more.

The wavelength scanning-type light source may be configured to emit light at a wavelength of about 700 nm to about 1,200 nm, with a tuning range of at least 1 nm.

The signal processing unit may be configured to make a calculation to output at least one parameter from among the axis direction length of the ocular axial length, corneal thickness, anterior chamber thickness, lens thickness, and retina thickness, the length of the horizontal corneal diameter (also called the "white-to-white" diameter) and pupil diameter in the cross direction, and the cornea curvature radius, from the resultant two-dimensional tomographic image.

The interferometer may be a free-space interferometer, and be configured such that the range for obtaining a sectional image by changing the light path length of the reference light is switched.

The signal processing unit may be configured to calculate the maximum of the signal strength or the average value as the cornea, the crystalline lens, and the border coordinate of the retina of the plurality of lines in a predetermined width range from the optical axis center from the acquired two-dimensional image.

The signal processing unit may be configured to calculate the curvature radius from position coordinates of three arbitrary points of the surface trace of the cornea.

The signal processing unit may be configured to calculate the degree of cloudiness of the lens found from either the difference of the reflectance level of the front and back of the lens or the ratio of the reflectance.

The ophthalmic optical tomographic image display device may be configured to additionally have a scan control unit to scan the two-axis tilt mirror in an x-axis and y-axis direction and change the scanning range to match the object to be measured.

The object lens of the probe may be configured to be attached to the optical axis to freely detach.

The probe may be configured to be a structure having a flexure-free main body

According to the present invention having such characteristics, scanning is enabled in the x-axis and y-axis direction using a parallel light beam, because the two-axis tilt mirrors are placed at the focus position of the object lens. Therefore, the coordinate of the optical axis direction is the same in the x-y plane when scanning regardless of the direction in the optical path, there is no need for the correction of the z-axis direction, and a two-dimensional image without distortion can be acquired. Therefore, this device, which is used for ophthalmology, allows the curvature radius of the cornea to be easily calculated.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The accompanying drawings, which are incorporated in and constitute a part of this specification, illustrate embodiments of the disclosed technology and together with the description serve to explain principles of the disclosed technology.

FIG. 3 is a waveform chart showing the scanning waveform of the x-axis direction and y-axis direction of two-axis tilt mirror being output by a scan control unit.

FIG. 11 is a diagram showing the front and cross section structure of an eye.

FIG. 24 is a graph showing a change in a reflective level at the center and the cross-sectional image in the first position according to the second embodiment of the present invention.

FIG. 26 is a diagram showing the change of light of the incident light in a first and second state according to the third embodiment of the present invention.

FIG. 28 is a diagram showing a usage example of the probe according to the fourth embodiment of the present invention.

REFERENCE NUMERALS

Figure 1:
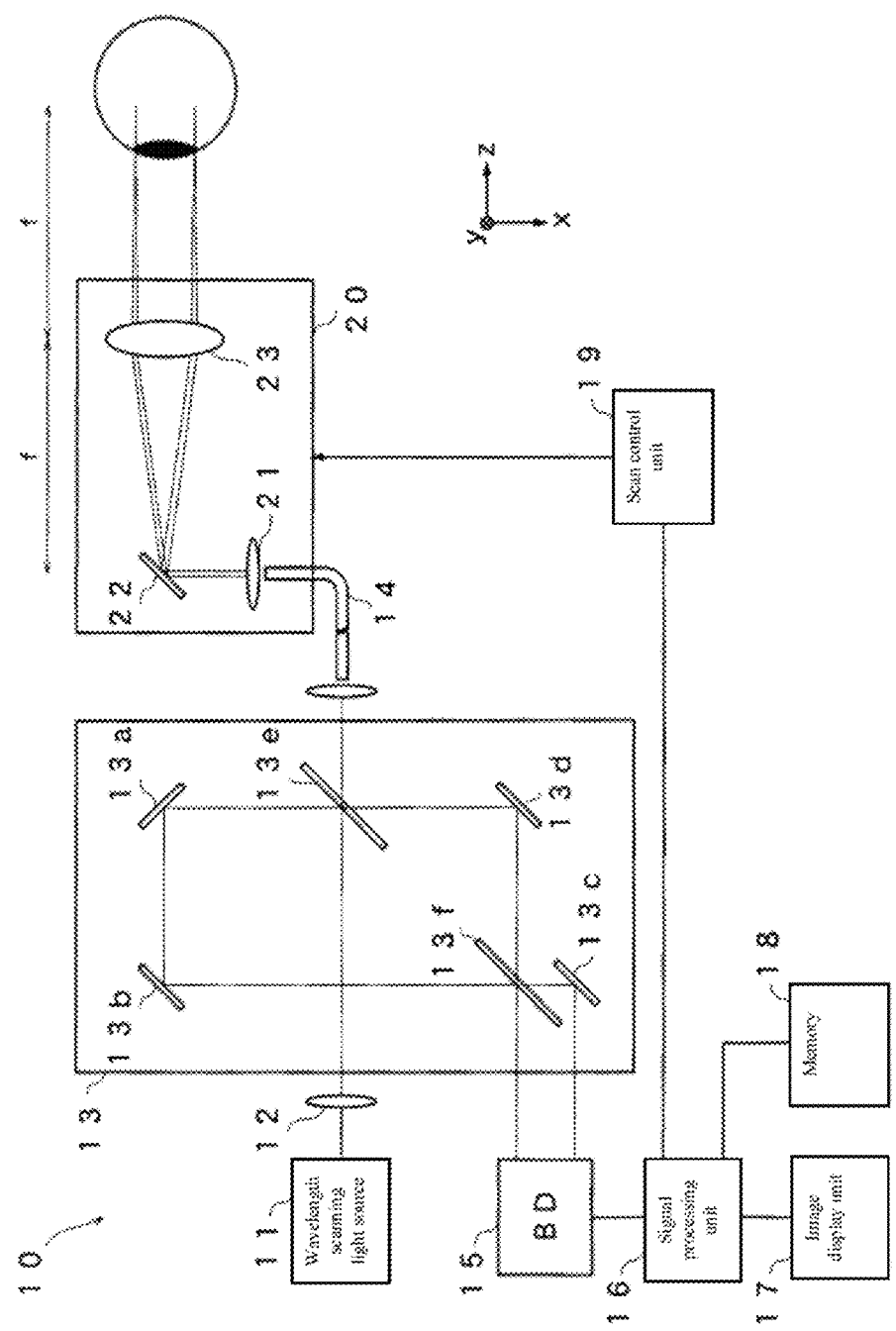
FIG. 1 is a block diagram showing the whole structure of the optical tomographic image display device of a wavelength scanning type according to the first embodiment of the present invention.

10. Optical tomographic image display device
11. Wavelength scanning light source
12. Collimator lens
13. Interferometer
14. Optical fiber
15. Balanced detector
16. Signal processing unit
17. Image display unit
18. Memory
19. Scan control unit
20. Probe
40, 47. Fixed parts
42, 46. Moving parts
44. Motor
45. Forwarding screw
48. Solenoid

DETAILED DESCRIPTION

FIG. 1 is a block diagram showing the whole structure of the optical tomographic image display device for of the ophthalmologic wavelength scanning type according to the first embodiment of the present invention. An optical tomographic image display device 10 in this diagram has a wavelength scanning-type laser light source. A wavelength scanning-type light source 11 outputs a laser beam with a periodically modified wavelength in the 700-1,200 nm band, for example, 1,060 nm, in a predetermined range of 1 nm or more, and preferably, in the range of 10 nm or more. Preferably the scanning speed should be, for example, 1 kHz or more, which is a velocity not subject to influence of the involuntary movement of an eyeball. The output of wavelength scanning-type light source 11 is provided to a interferometer 13 via a collimator lens 12. The interferometer 13 should be a Mach-Zehnder interferometer of a space type combining mirrors 13a, 13b, 13c, 13d, and half mirrors 13e, 13f. In the interferometer 13, a part of the light applied to the half mirror 13a is reflected and applied to a half mirror 13f as a reference light via mirrors 13a and 13b. The light remaining from out of the lights applied to the half mirror 13e is emitted by the half mirror 13e, and transmitted to the probe side 20 to be described later via a single-mode optical fiber 14. Further, a reflected light from a probe 20 is incident on the half mirror 13e of interference meter 13. Part of the reflected light incident on the half mirror 13e from the probe 20 is further reflected, applied to the mirror 13f via the mirror 13d, and interferes the light. Here, the sample light is arranged from the output position of the half mirror 13e to the half mirror 13f through an imaging range of 0 point; and the reference light is arranged from the output position of the half mirror 13e to where the waves meet by the half mirror 13f passing the course on the side of the reference mirror through mirrors 13a and 13b. Thus, they are arranged so that they will become the same light path length, respectively. Here, the interference light is incident on a balanced detector (BD) 15. The balanced detector 15 converts the light signal into an electrical signal and the output is applied to a signal processing unit 16. The signal processing unit 16 has an amplifier, a low pass filter, and an AD converter, which are not shown, in the interior, to generate a cross-sectional image by Fourier transform based on frequency change and intensity of the reflected light, and the image is displayed on an image display unit 17. Moreover, memory 18 and a scan control unit 19 are connected to the signal processing unit 16. Memory 18 maintains a calibration table or the like, to be described later, and the scan control unit 19 applies the scanning signal to the probe 20, to be described later.

Figure 2:
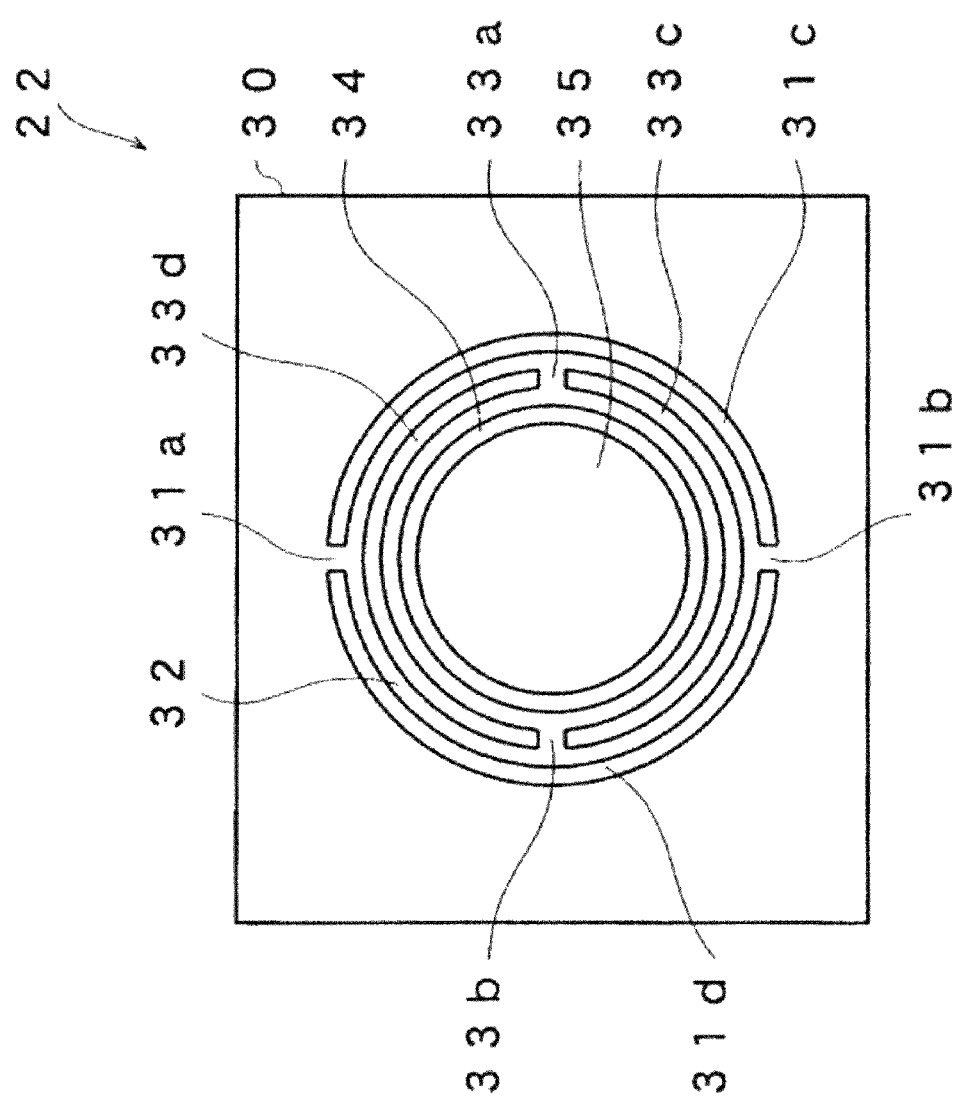
FIG. 2 is a front view of MEMS mirror with two-axis tilt mirror used in the present embodiment.

Next, the structure of the probe 20 is described. The probe 20 as shown in FIG. 1 has a collimator lens 21 and a two-axis tilt mirror 22 on an optical axis of the optical fiber 14, and emits the light reflected from the two-axis deflecting mirror 22 to an object to be measured through an object lens 23. Assuming the focal length of an object lens is f, the two-axis tilt mirror 22 is arranged at the focal position of the object lens 23, and will reflect light in the two-axial direction of x-axis and y-axis from the same position. In the present embodiment, the two-axis tilt mirror 22 is implemented through the two-axis tilt mirror having an MEMS structure. FIG. 2 is a front view of the two-axis tilt mirror 22 having this structure. In a base 30 around the two-axis tilt mirror 22, there are circular grooves 31c, 31d, except in the hinge regions 31a and 31b, as shown in FIG. 2, and a vibration range 32 is provided to the center. Within this vibration range 32, there are, except in hinge regions 33a and 33b, circular grooves 33c, 33d in the perpendicular direction to hinge regions 31a, 31b, with a vibration range 34 is formed in the center. Further, there is a circular reflecting region 35 inside the vibration range 34. A line that connects the hinge region 33a and 33b and a line connecting the hinge region 31a and 31b are at a right angle, hereby allowing the axis of rotation to be at a right angle, and can scan the light in the x-axis direction and the y-axis direction from the same position. In order for the scan control unit 19 to control the angle of reflecting region 35 at the center, a control signal for inclination angles in the x-axis direction and y-axis direction is inputted into the two-axis tilt mirror 22.

Next, the two-axis tilt mirror 22 in the probe 20 is arranged at the focal position behind the object lens 23. Then, since a beam scan that is always parallel in the x and y directions, in other words, a beam scan that is telecentric can be obtained by carrying out a two-dimensional scan, the coordinate of the optical axis (the z-axis) direction is the same as in an x-y plane despite which direction the light is scanned at least in regards to optical telemetry. Thus, a three-dimensional correction becomes unnecessary. As for MEMS, the light can be scanned in a linear manner by the two-axis tilt mirror 22. If the object lens also has little aberration, the image acquired will become an image without the right distortion only by applying the coefficient of a simple scale.

Next, the scan control unit 19 is further described. FIG. 3(a) is a sine wave-like scanning signal for controlling the two-axis tilt mirror 22 in the x-axis direction, and FIG. 3(b) shows a control signal for scanning in the y-axis direction on the same temporal axis as this. The period of these scan signals becomes an integral multiple, and the scan is carried out in the x direction and y direction. By this means, it can scan in the x direction and y direction.

Figure 4:
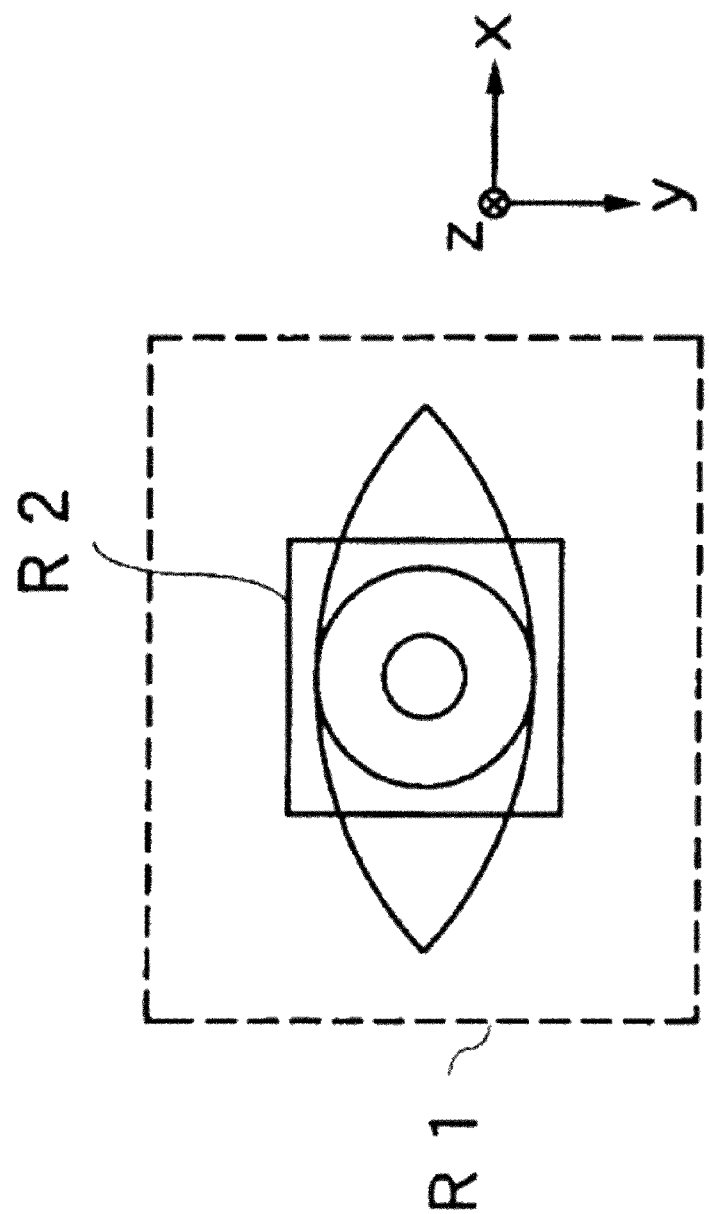
FIG. 4 is a diagram showing the measurement region and the deflectable region when scanned using the signal of FIG. 3.

With a normal ophthalmology device, the head part of the device was moved to the position of the eye of the patient to match and align the position of the eye with the center of a camera or probe. However, even if the device is roughly aligned and fixed, the position of the eyeball is usually not constant since the position of the eyeball of each patient is different. Therefore, much time was needed to perform precise alignments. In this embodiment, therefore, the effective diameter of an actual object lens 23 is set to two to three times larger than the actual measurement range. A rectangular region R1 as shown in FIG. 4 with a dashed line is set as the deflectable range which is capable of scanning light through the object lens 23. Then, assuming the eye of the patient is located in the front center of the object lens 23 as shown in FIG. 5(a), only a measurement region R2 where the eyeball is located as shown by the solid square line in FIG. 4 can be scanned by lowering the amplitude of vibration of the scanning signal to the y-axis direction and x-axis direction, as shown in FIG. 3, with a central focus on $V_{x1}$ and $V_{y1}$.

Figure 5:
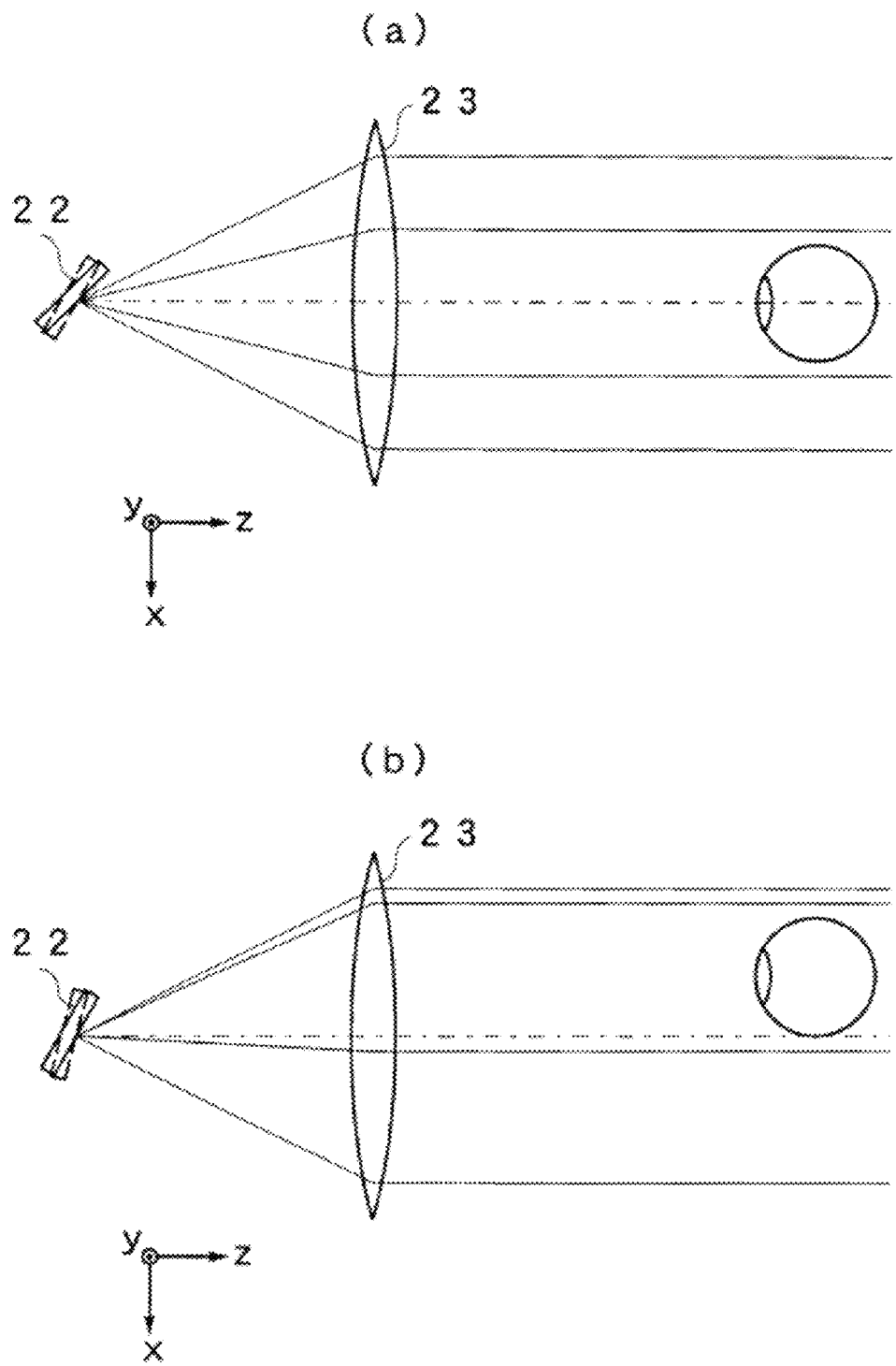
FIG. 5 is a diagram showing the relationship among the measurement region, the deflectable region and the measuring object.
Figure 6:
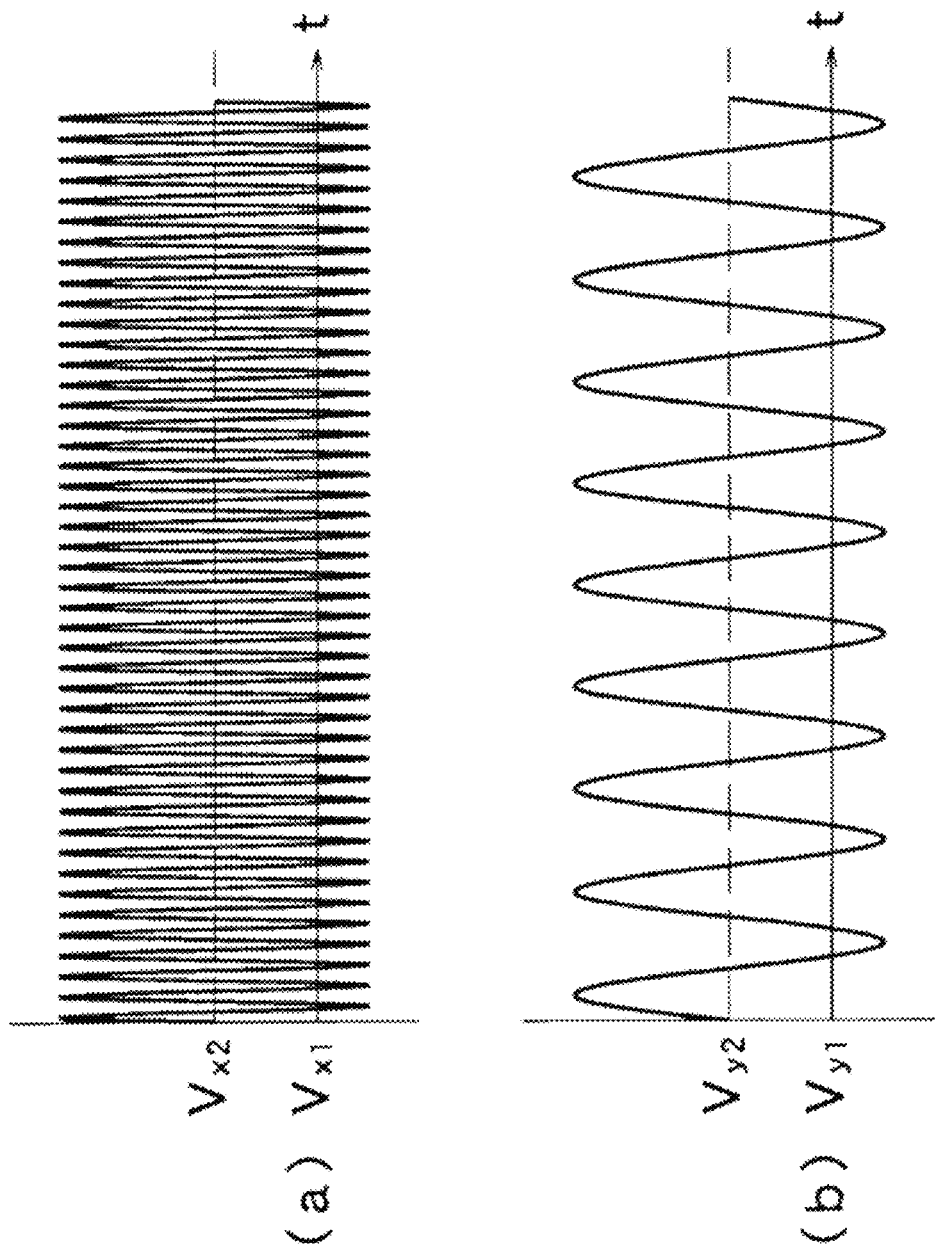
FIG. 6 is a diagram showing the other scanning waveform of x-axis direction and y-axis direction being output by a scan control unit.
Figure 7:
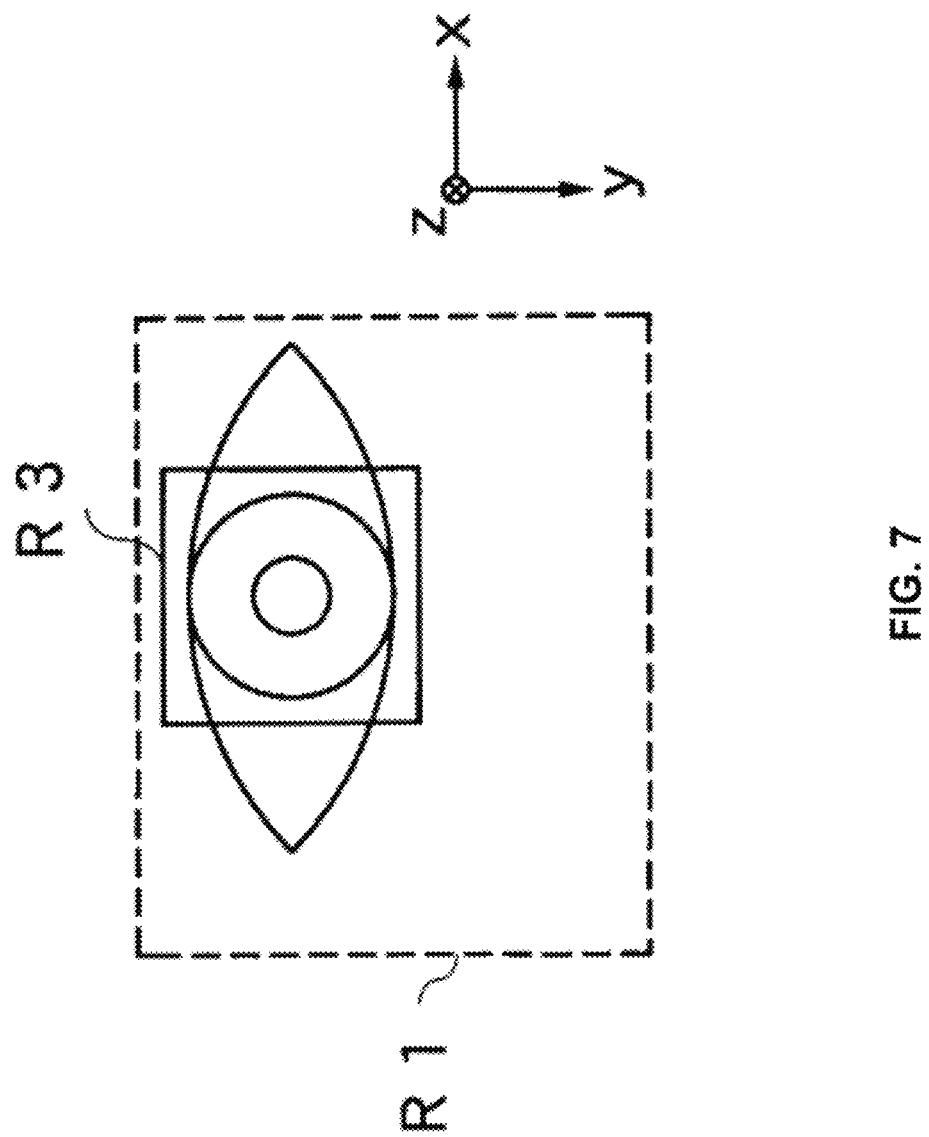
FIG. 7 is a diagram showing the measurement region and another position of the eyeball inside the deflectable region.

Here, when the position of the eye of the patient deviates from the center as shown in FIG. 5(b), an offset is added to the voltage to impress it on an MEMS mirror as shown in FIG. 6, and for example, the amplitude of vibration of the scanning signal to the x-axis direction and the y-axis direction, a scanning signal with a central focus on $V_2$ and $V_2$. When carried out in this manner, the measurement region R3 can be offset as shown in FIG. 7, and only the range where the eyeball is located can be scanned. This adjustment allows the adjustment of the deflected position to be performed extremely easily by only changing the offset of the scanning signal to two-axis tilt mirror 22, which outputs from the scan control unit 19.

Next, the operation of the optical tomographic image display device is described according to the present embodiment. As described above, the distortion of the image is constant for the z-axis direction in this embodiment. There is little need to correct the distortion; however, a change in position is non-linear in terms of time just by slightly scanning with the MEMS mirror and distortion occurs in the x-axis direction and the y-axis direction due to the distortion in the object lens 23. Since these are distortions of the x and y directions, if the calibration value of a certain one x, y plane can be obtained, all the other data may be calibrated with the same calibration value. Therefore, before the normal operation, calibration of the probe must be performed.

Figure 8:
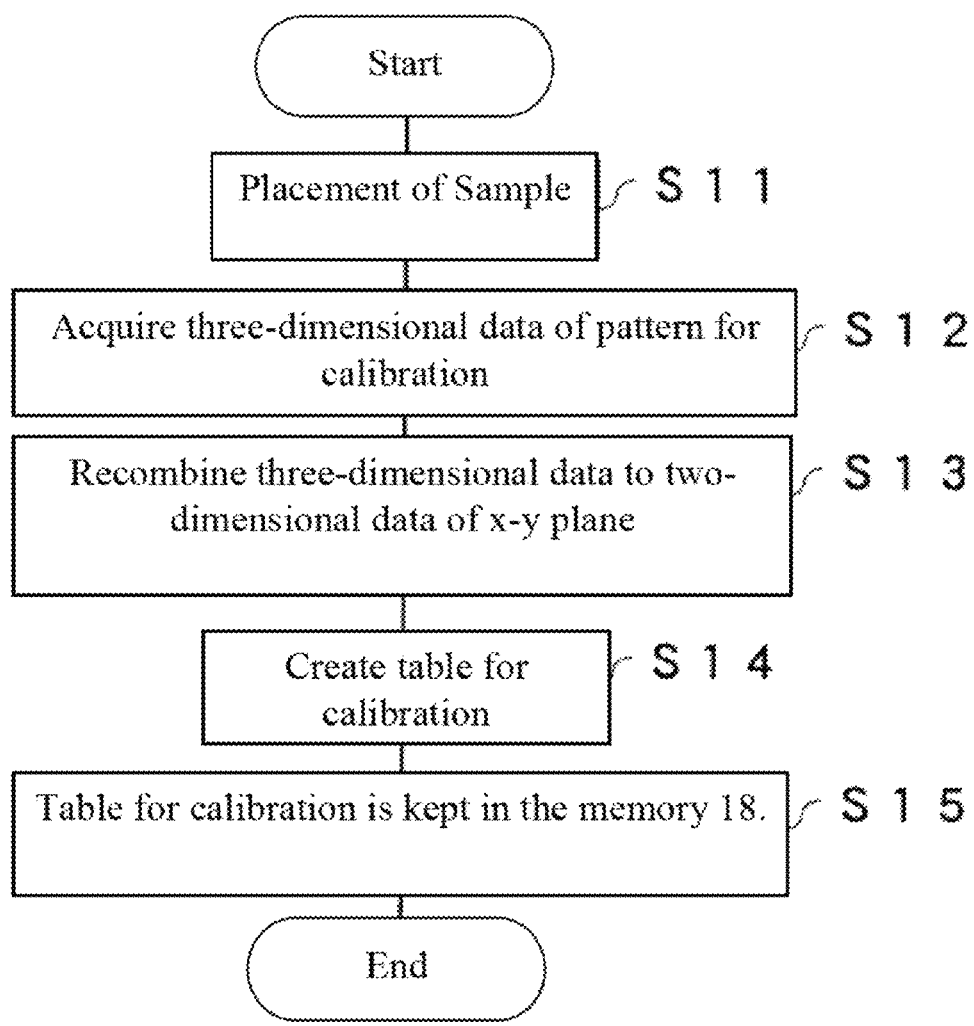
FIG. 8 is a flowchart showing the processing at the time of probe calibration of the present embodiment.
Figure 9:
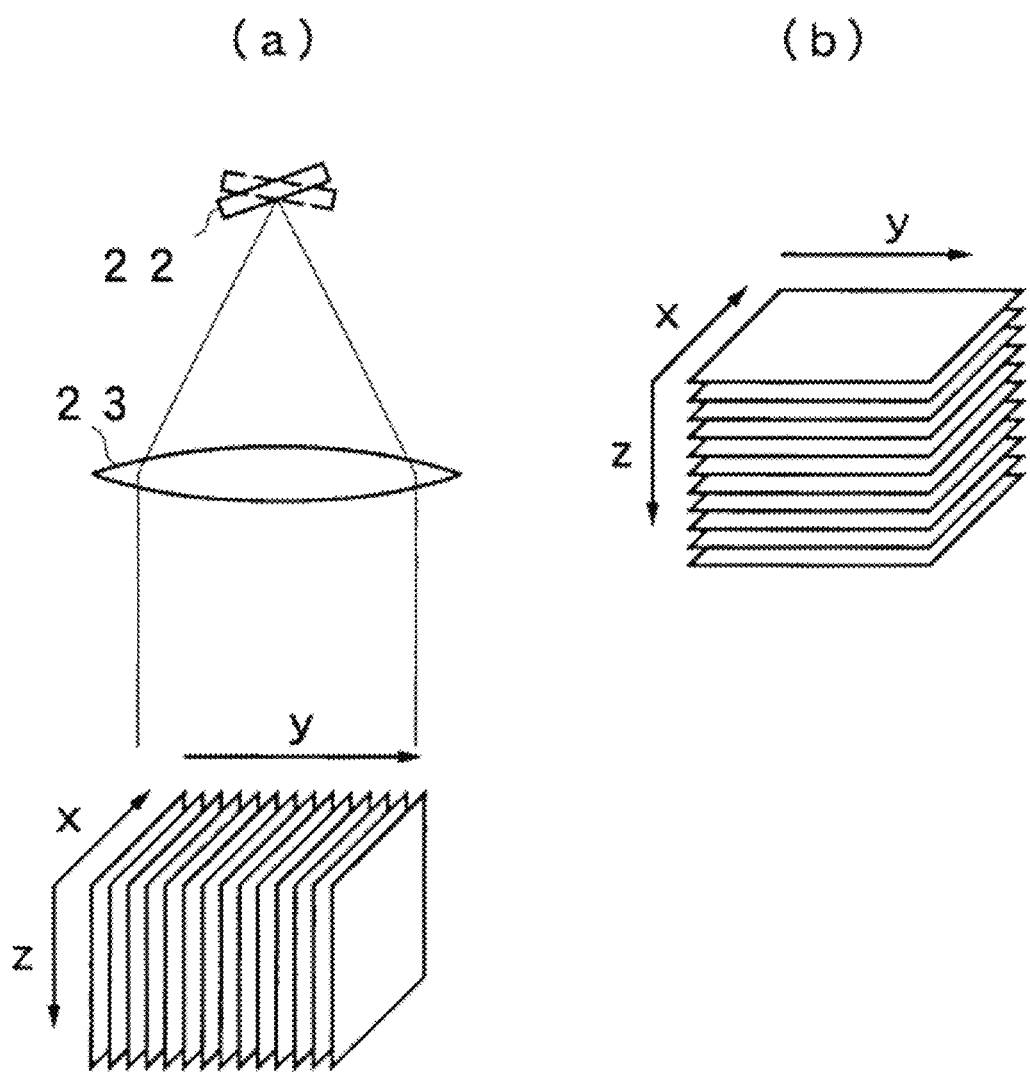
FIG. 9 is a schematic view showing the probe calibration processing of the present embodiment.

FIG. 8 is a flowchart showing the processing of the probe calibration, and FIG. 9 is a diagram for describing an outline of a calibration. First, a sample for calibration, such as a grid pattern in which the cross-sections at the position to be measured are all known, is placed at Step S11. Then, when wavelength scanning light source 11 is operated, the emitted light from the wavelength scanning light source 11 becomes a parallel beam with the lens 12, and enters the interferometer 13. The light that continues diverging with the half mirror 13e transmits into the sample side, and the other reflects to the mirror 13a side. Next, the reference light and reflected light obtained from the sample are combined by the half mirror 13f, and the interfering light is balance detected by the balanced detector 15. Further, Fourier transform processing is carried out by the signal processing unit 16, and an image is displayed with the image display unit 17.

In step 12, the two-axis tilt mirror 22 is tilted to scan in the x-y direction, and three-dimensional image data (x, y, z) are extracted. As shown in FIG. 9(a), many cross-sectional images of the x, z plane can be obtained along the y-axis direction when carried out in this manner. In step S13, as shown in FIG. 9(b), the three-dimensional image are reconstructed to become many cross-sectional images along the z-axis direction based on the images of the x, y plane from the three-dimensional data, and become the two-dimensional images (x, y) with different depths taken at predetermined distances. In step S14, a calibration parameter table is created to have the two-dimensional table cancel the distortion on the predetermined x-y plane. More specifically, if the difference ($\Delta x_{ij}$, $\Delta y_{ij}$) between the distorted grid (i, j) and the correct grid (i, j) is found, then it becomes the revised coefficient of the image, and the compiled data of each image of the x, y plane becomes the calibration table. As described above, the distortion of the image is constant in the z-axis direction; and is only for the x-y plane. Therefore, if a calibration table is created only for the x-y plane, then the data can be corrected using the same calibration table of the image data of the x-y plane having other depths. In step S15, this calibration table is maintained in memory 18 by the signal processing unit 16. When carried out in this manner, this revised coefficient can be used to correct a coordinate with regards to an arbitrary coordinate which has been photographed.

Figure 10:
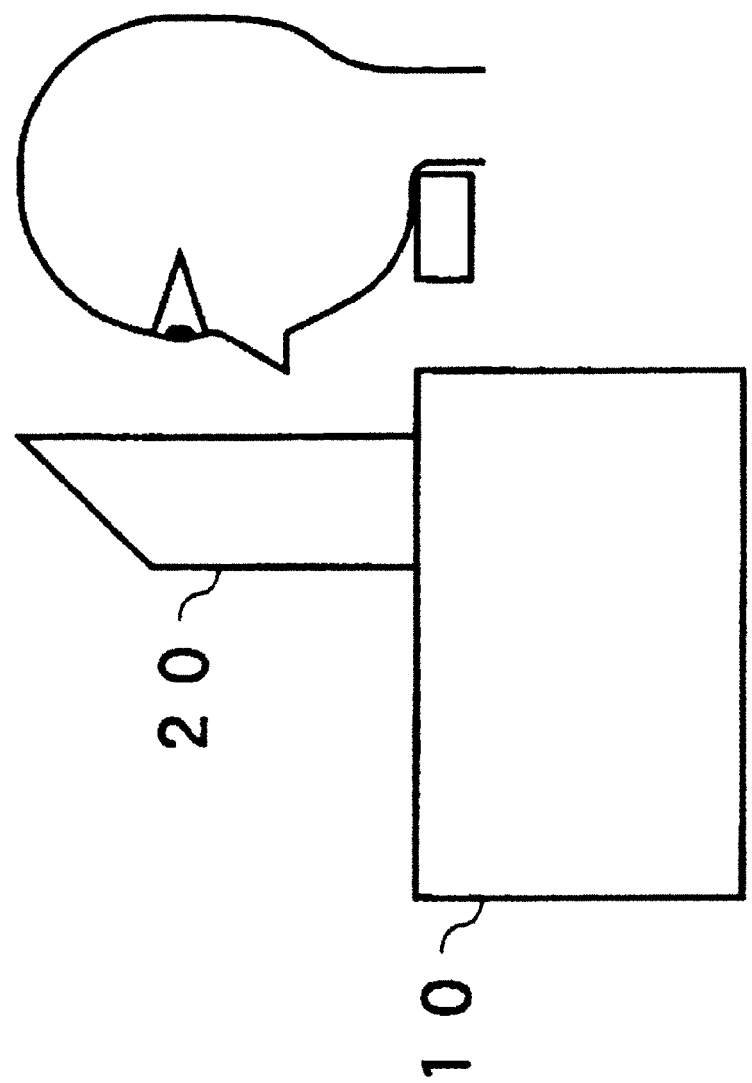
FIG. 10 is a schematic view showing the state when the human eye is measured.

Next, the data processing for measurements and tomographic display after calibration processing was carried out is described. First, as shown in FIG. 10, a probe is installed so that the human body to be measured is located in the region where the light is emitted from the probe 20, and the wavelength scanning light source 11 is started. Next, as shown in FIG. 3 and FIG. 6, an offset is added to the scanning signal if necessary and the deflected position of the light beam is moved to correspond to the desired scanning region. Then, the region of the required image is scanned in the x-axis direction and y-axis direction by the scan control unit 19. Therefore, in the normal ophthalmology device, it isn't necessary to move the head part of the device with a common joystick to match and align the center of the eye with the center of the camera. In other words, it is not necessary to be equipped with an alignment mechanism and the device can be miniaturized. When carried out in this manner, a three-dimensional image data of the eye of the patient can be obtained. FIG. 11(a) is cross sectional example of an eye, and FIG. 11(b) is a view from the front.

Figure 12:
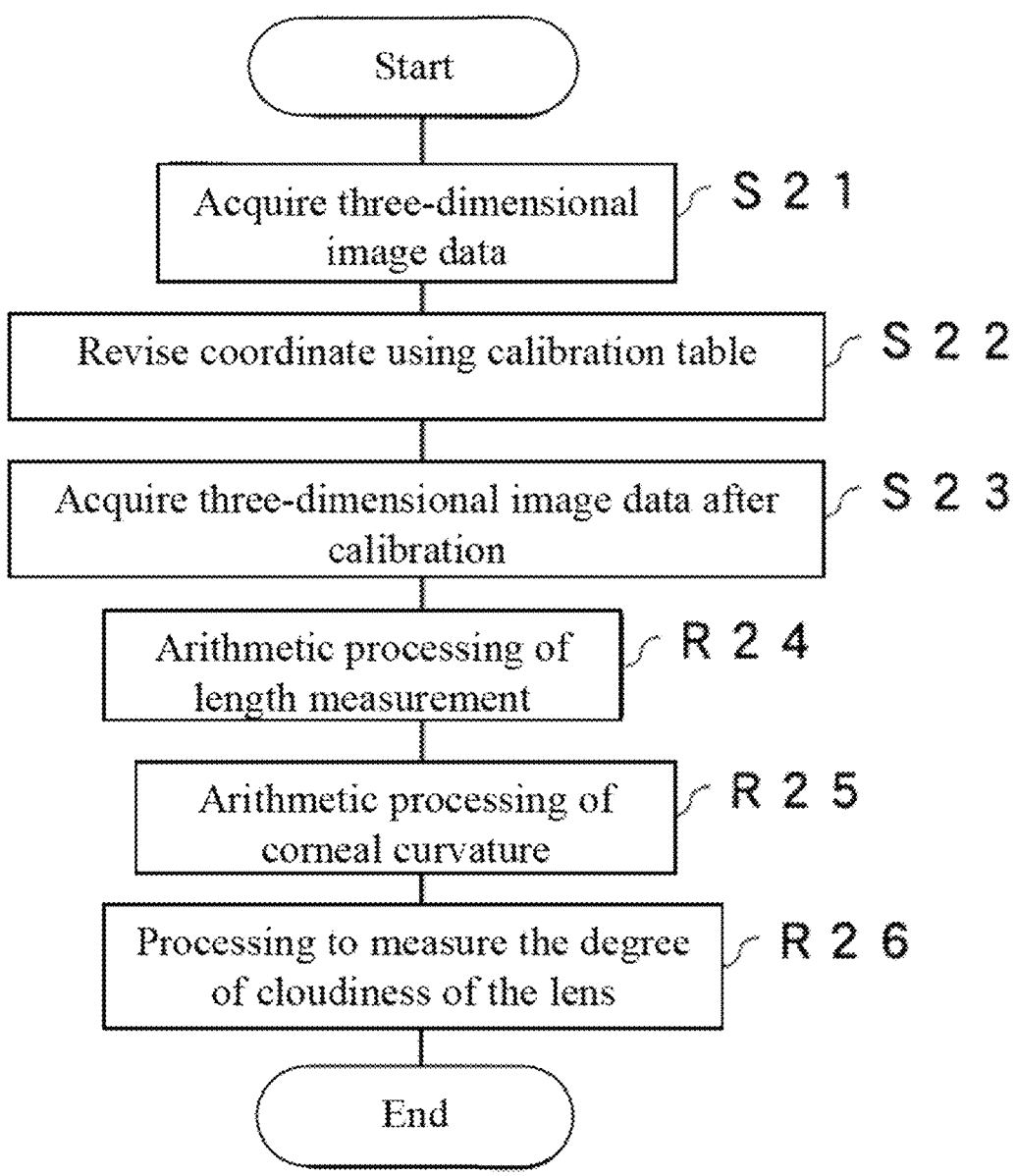
FIG. 12 is a flowchart showing the operation at the time of usage of the present embodiment.

Next, the data processing for measurements of the present embodiment will be described in which various measurements are taken using the obtained images. FIG. 12 is a flowchart showing this processing. In the same drawing, in step S21, first, three-dimensional data is acquired in the same manner as a case of the calibration processing mentioned above. In this case, a probe of this measurement device is made to approach the eyeball of the patient to have the eyeball measured, and the wavelength scanning-type light source is started. Next, the calibration table in steps S22, S23 is used to correct the coordinate position after having acquired the three-dimensional image data of the object to be measured. Three-dimensional data without distortion can be obtained when carried out in this manner. Then, a processing for measuring the length of an eyeball to be measured is performed based on the three-dimensional data in a routine R24. In addition, a curvature arithmetic processing for a cornea is performed in a routine R25. Further, a processing for measuring the degree of cloudiness of the lens is performed in a routine R26, and the processing ends.

(Processing for Length Measurement)

Figure 13:
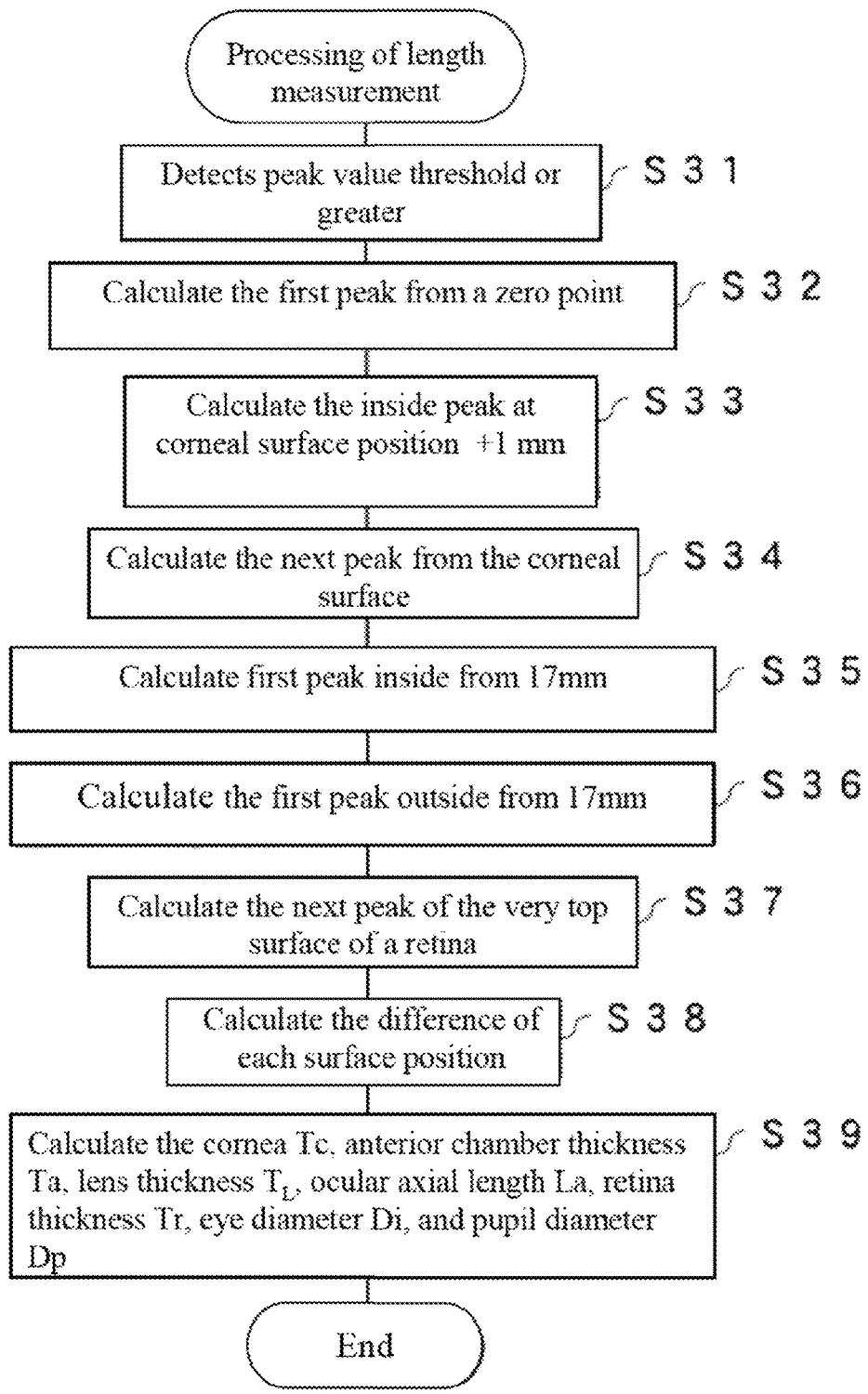
FIG. 13 is a flowchart showing the arithmetic processing of length measurement of the present embodiment.

Next, the details of the routine R24 for measuring length will be described while referring to the flowchart in FIG. 13. As shown in the cross-sectional view of FIG. 11(a), the various kinds of parameters needing measurements include, for example, an ocular axial length La, a corneal thickness Tc, an anterior chamber thickness Ta, a lens (the crystalline lens) thickness $T_L$, and a retina thickness Tr. Furthermore, a corneal diameter Di and a pupil diameter Dp, which is the diameter of the pupil, are measured as shown in FIG. 11(b). Because the internal structure of the eyeball needing to be measured is almost transparent, each surface signal becomes the peak value which basically allows them to be detected in order. However, the inside of the cornea has a brightness caused by the dispersion of the cornea cells, and the borders of the nuclei inside can be seen due to the nuclei inside the crystalline lens. In addition, it is necessary to make a detection to make sure it is correct, since there are peaks other than that of the object to be measured which are not necessary. The cross-sectional image can be measured by drawing a line by hand using a line marker; however, by knowing the structure of the eyeball and the thickness range of each of the tissues, only the necessary surface signal can automatically be selected at a certain constant step and the position can be found.

Since it is well known that the human eyeball is generally within a predetermined range, this knowledge can be used to calculate and improve the precision of the necessary parameters. For example, the range of the corneal thickness Tc is 0.3-0.8 mm, the anterior chamber thickness Ta is 1.5-5.5 mm, the lens (the crystalline lens) thickness $T_L$ is 3-6.5 mm, and the ocular axial length La is in the range of 14 mm-35 mm. Therefore, knowing that the back side of the cornea is the cornea surface +1 mm, the surface of the lens is next after the cornea back side, the back side of the lens is always in front (<La/2) from the half position of the ocular axial length and the retina is the cornea surface +14 mm or more, other peaks and false detection related to noise can be reduced when screening measurements.

Figure 14:
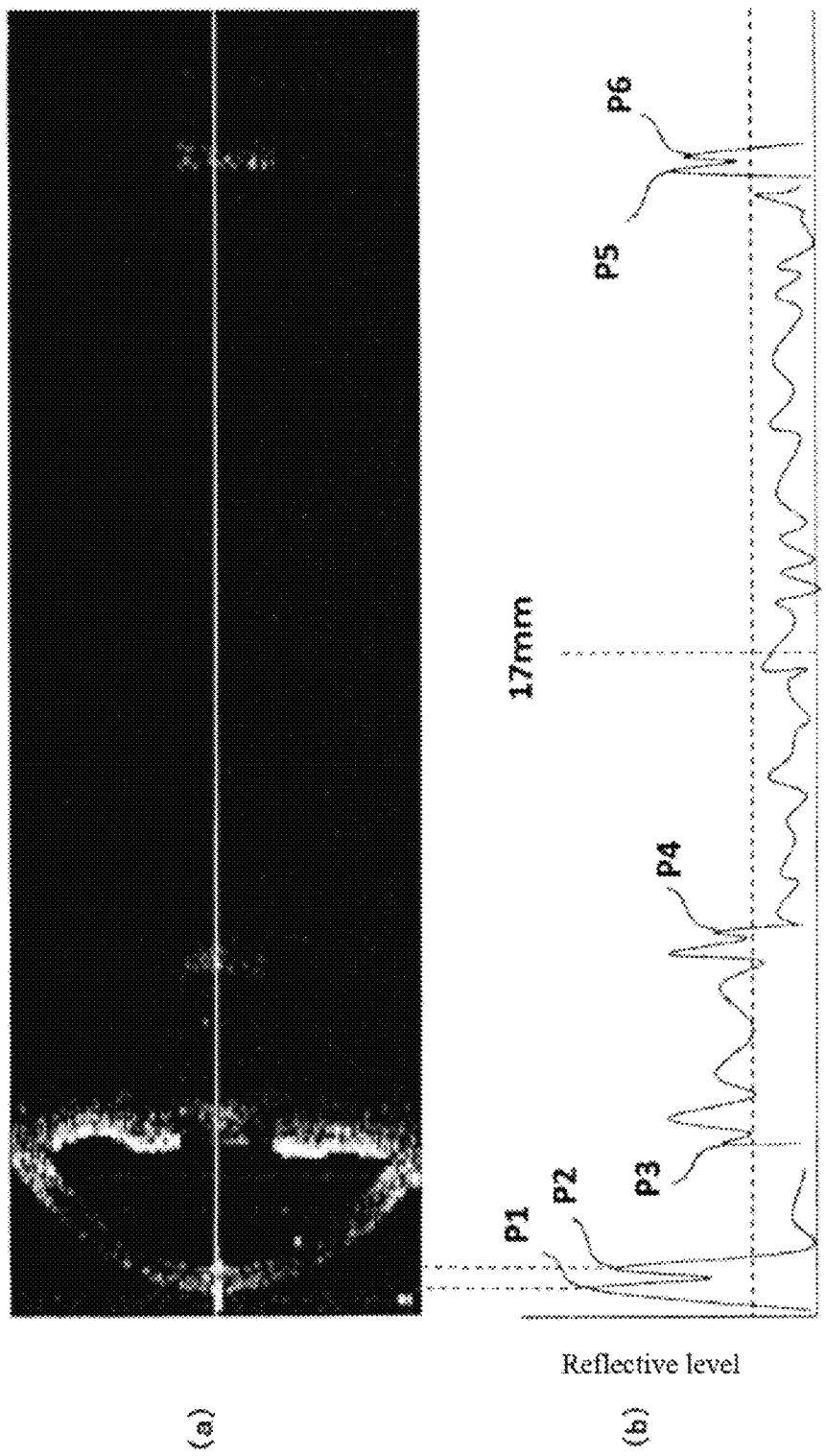
FIG. 14($a$) is a diagram showing an example of a dislocation in an x z direction, and FIG. 14($b$) is a graph showing a change of central brightness of this dislocation.

FIG. 14(a) is a diagram showing the cross-sectional image of xz cross-section of the human eye, and FIG. 14(b) is a graph showing a reflective level of the centerline. In step S31, the peak value of the vicinity of zero point of the z-axis is detected. At this time, the predetermined value from the noise level, for example, a level of 5 dB or more, is set as the threshold, and the plurality of peak values exceeding the threshold is detected by differentiation, etc. In step S32, the position of a first peak P1 is calculated from zero point (Z=0). The surface position of the cornea can be decided by this peak P1. In step S33, the position of a peak P2 on the inside, which is around +1 mm bigger than the cornea surface position, is calculated. Hereby the cornea back side position can be defined. Next, the position of a peak P3 further inside from the cornea back side is calculated. Hereby, the crystalline lens surface position can be defined. In step S35, the position of a first peak P4 that is 17 mm closer to the inside from the zero point is calculated. Hereby, the back side position of the crystalline lens can be specified. In step S36, the position of a first peak P5 that is 17 mm closer to the outside is defined. Hereby, the position of the outermost surface of the retina can be calculated. In step S37 next, the position of the outermost surface peak P6 of the retina is found. Hereby, the position of the retina epithelium, can be decided. In step S38, the difference of each surface position is calculated in consideration of the refractive index. The ocular axial length La, corneal thickness Tc, anterior chamber thickness Ta, lens thickness $T_L$, and retina thickness Tr are calculated based on the data acquired in this manner. In addition to this, the corneal diameter Di and pupil diameter Dp are measured from the x-y image of the vicinity of the cornea.

Figure 15:
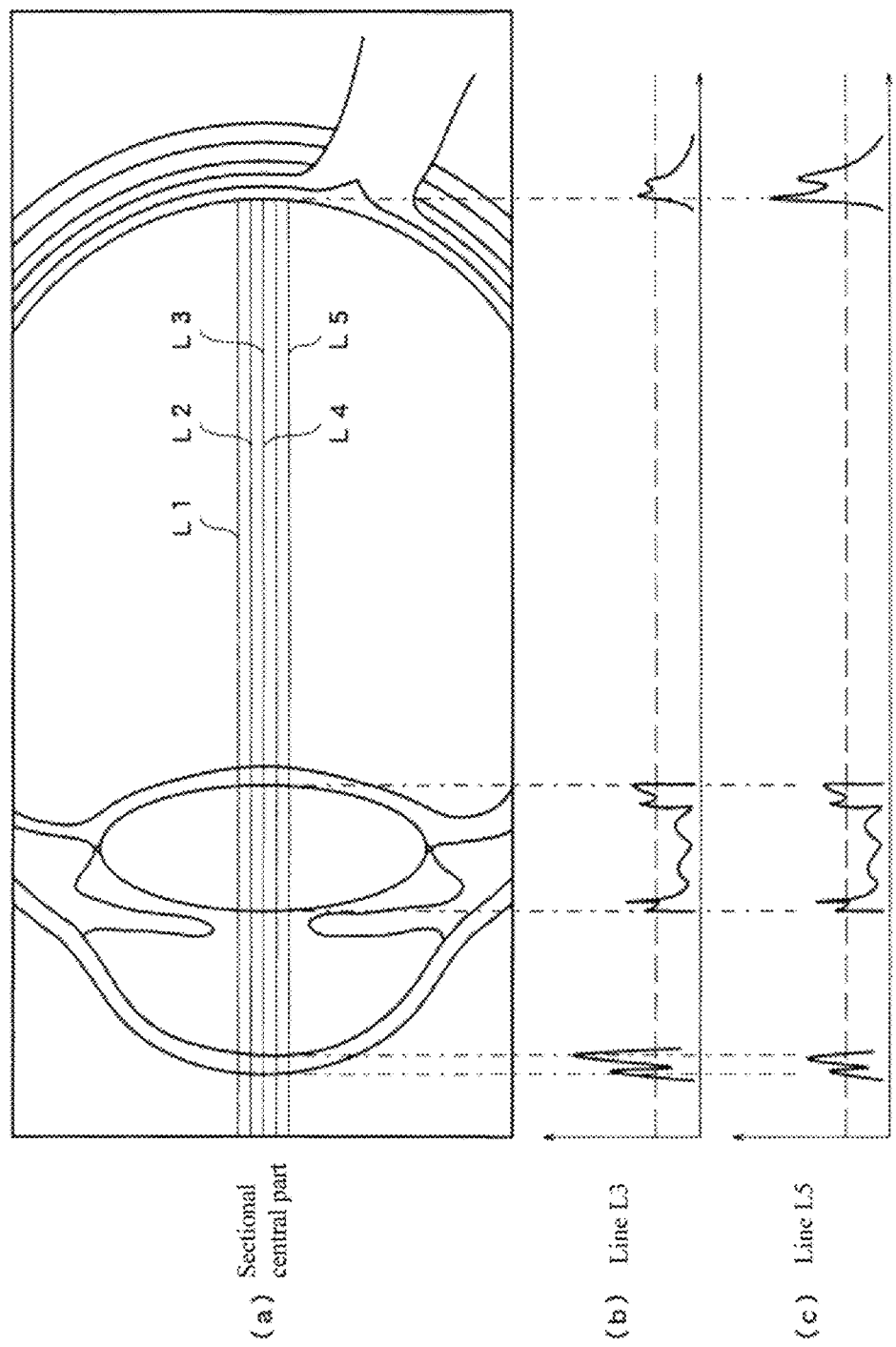
FIG. 15 is a graph showing a change of brightness on the line of plural z-axis directions and a schematic view of an optical tomographic image.

Moreover, the peak value is calculated by the change of the brightness of the central line, and each parameter is calculated; however, each of the boundary surfaces do not all have the same constant strength when a two-dimensional image has been acquired, and there are times when omissions occur. Therefore, from the center, for example, in the range of ±0.5 mm, since each boundary surface is almost flat, even if the level of the reflected light of the plurality of lines within the range is selected as the data for position sensing at the position of the peak where the strength is the highest for each, the measurement data can be sufficiently used. From the acquired x-z cross-sectional images, the maximum of the signal strength of the plurality of lines in a certain range from the optical axis center can be calculated as the border coordinate of the cornea, the crystalline lens, and the retina. For example, with the centerline being L3 as shown in schematic view in FIG. 15(a), the brightness of lines L3, L1 and L2, which are before and after it, and L4 and L5 are the objects to be measured. Of these, FIG. 15(b) is the brightness signal of the centerline L3, and FIG. 15(c) is a graph showing the brightness signal of the line L5 which is −0.5 mm away from the center. When the brightness of each line of these pluralities of brightness signals is the threshold or greater, the position from the peak data of the plurality of line portions can be detected. In the example of FIG. 15, the peak values of the surface and the back side of the cornea detected by the center line L3 are high, and the peak value of the outer most surface of the retina detected by line L5 is high. In this way, by adopting the position showing the higher peak as the position data, even if a portion of some lines is missing, the position of each peak value can be even more precisely determined.

Moreover, in this embodiment, the plurality of lines L1-L5 which are higher than the peak value of each position are selected; however, the position of the peak is calculated based on the average value of the plurality of lines, and the ocular axial length may be measured based on this.

Errors caused by movements of the patient can be nearly eliminated since the calculation of such peak values and the detection of each parameter are completed in an extremely short period of time.

Arithmetic Processing of Corneal Curvature

Figure 16:
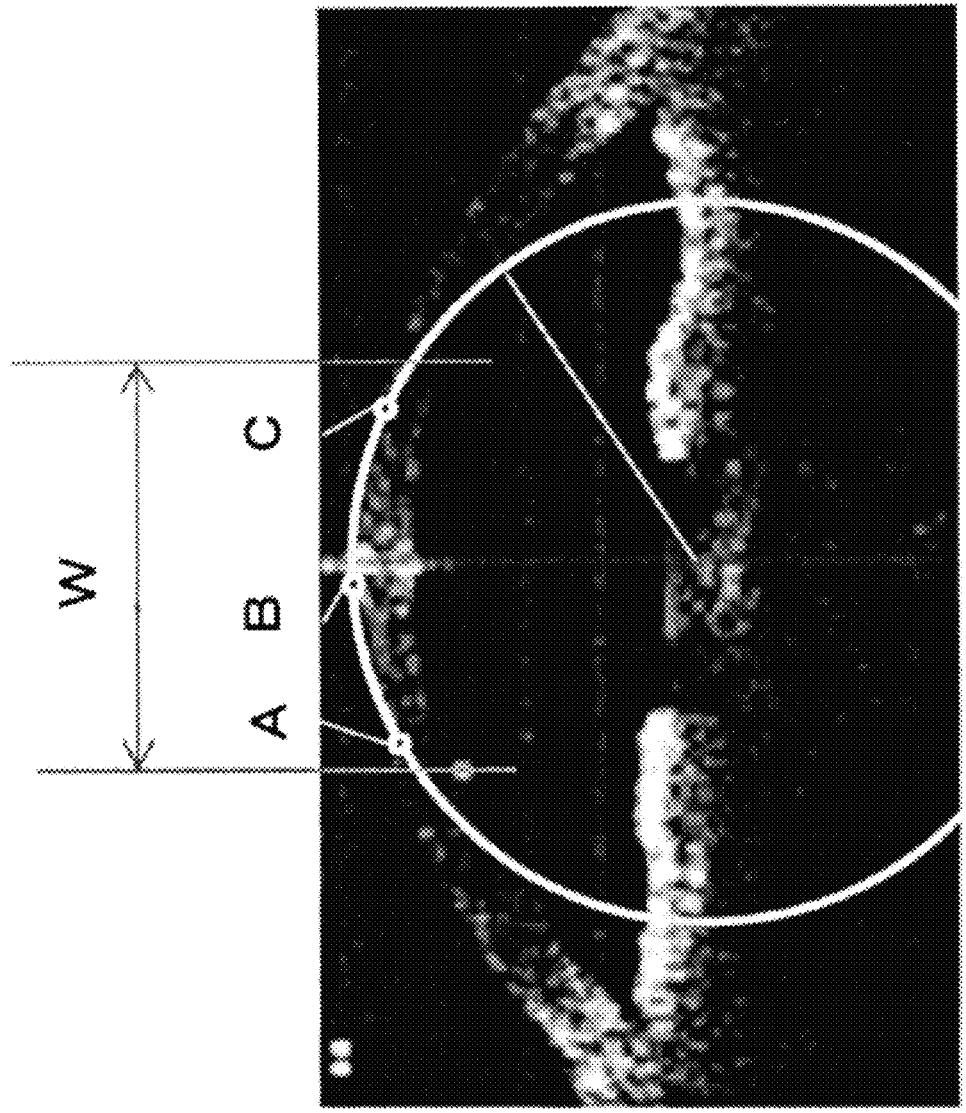
FIG. 16 is a diagram showing an example of a cross-sectional image around the cornea.
Figure 17:
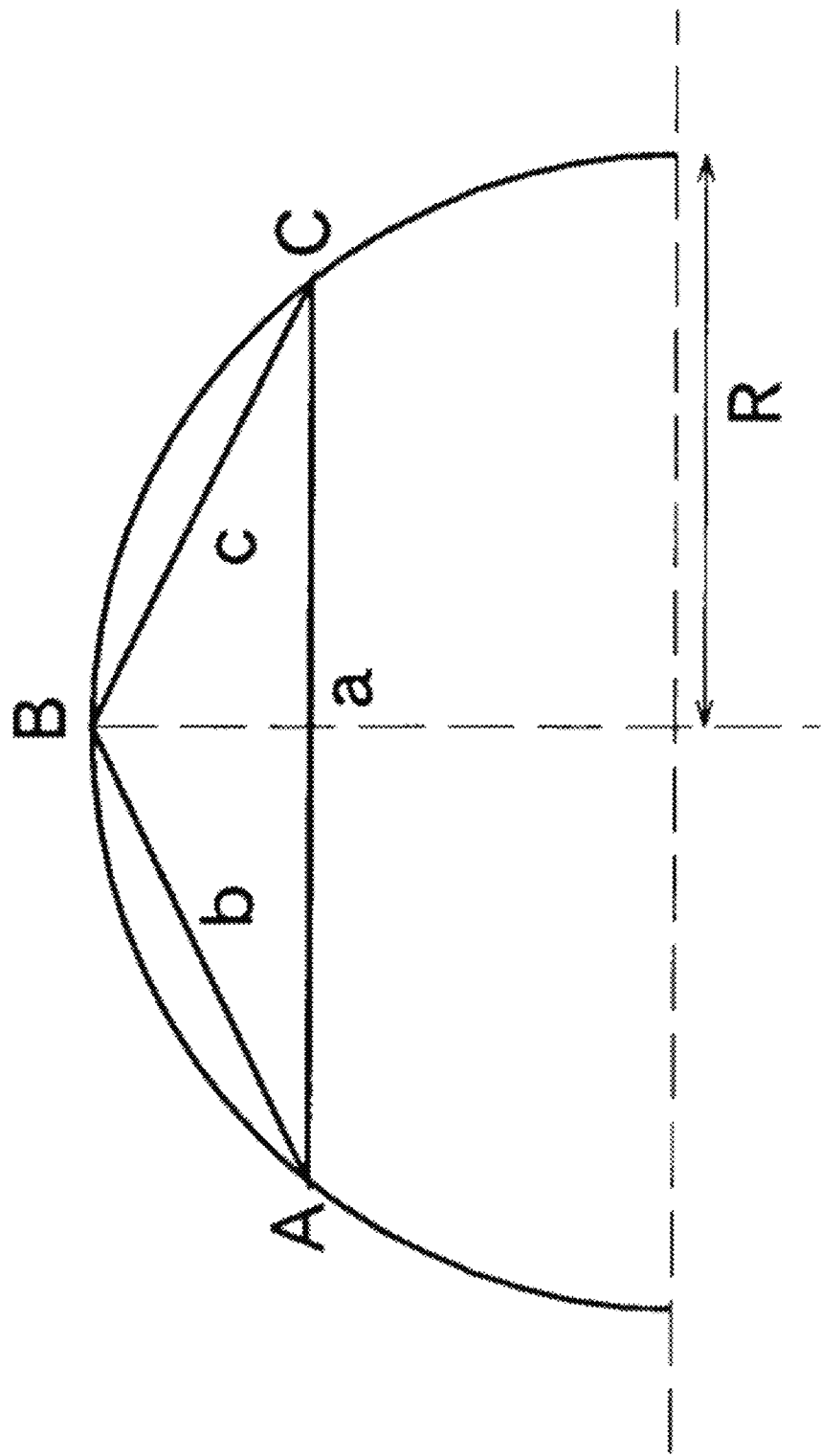
FIG. 17 is a diagram showing the relationship of a curvature radius and each side when the curvature radius is measured from three points.

Next, the arithmetic processing of the corneal curvature of the routine R25 will be described in detail. Here, the signal processing unit 16 finds the curvature from the position coordinate of the three arbitrary points of the surface trace of the cornea. For example, in FIG. 16, the coordinates of arbitrary points serving as the cornea surface will be A, B, and C. The three arbitrary points are extracted from the effective range W (for example, range of 2 or 3 mm including the center) to detect the curvature radius of the cornea surface. Then, the curvature radius on the plane going along the three points can be calculated by calculating the curvature radius. Therefore, the calculation speed can be improved in comparison with conventional methods. In this case, as shown in FIG. 17, assuming the length of each side of a triangle, in which these points A, B, and C are the tops, are a, b, and c, the radius R of the circle in contact with the triangular top is found from the theorem of the following geometric circumscribed circle using the following expression:

$$R = \frac{abc}{\sqrt{(a+b+c)(-a+b+c)(a-b+c)(a+b-c)}}$$

In order to increase the measurement precision of the curvature radius, it is preferable to extract the three arbitrary points many times and calculate the radius based on this, and find the curvature radius by calculating the average value.

Figure 18:
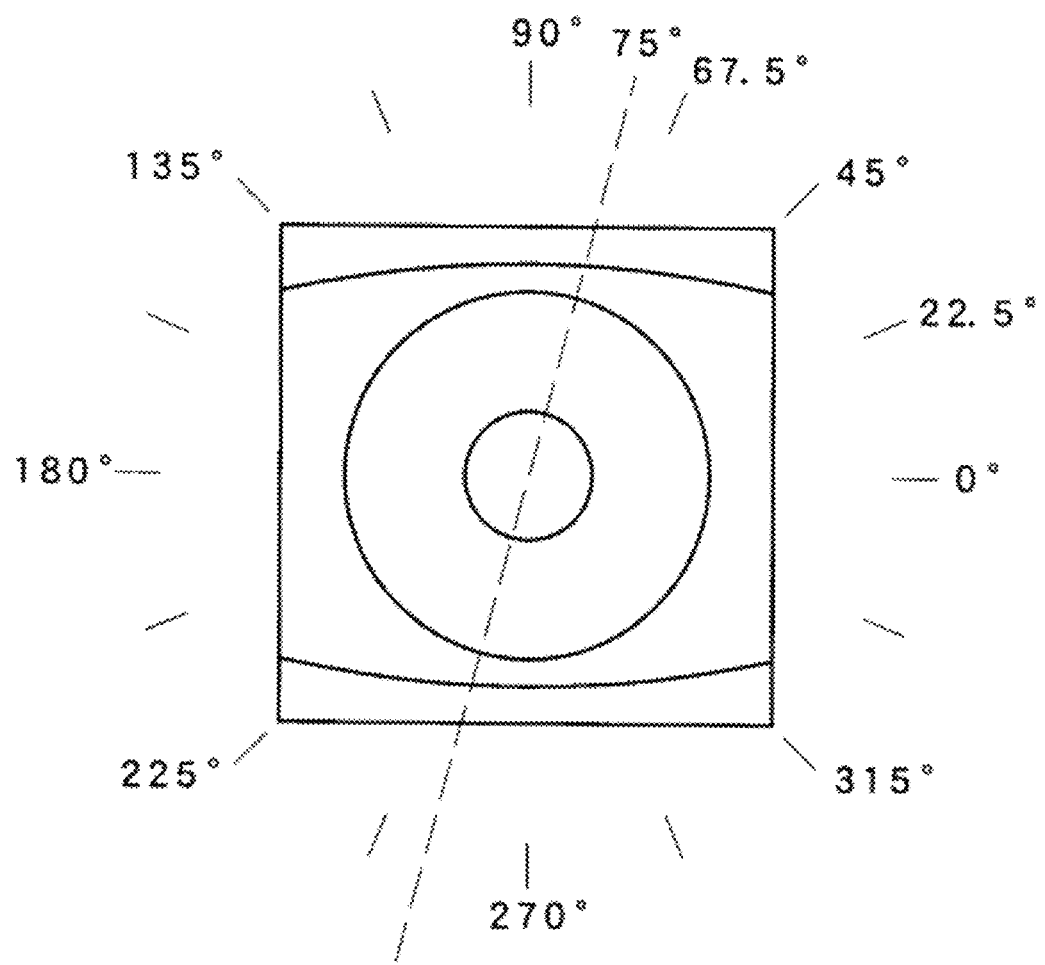
FIG. 18 is a diagram showing the surface of an eye when viewed from the cornea side.
Figure 19:
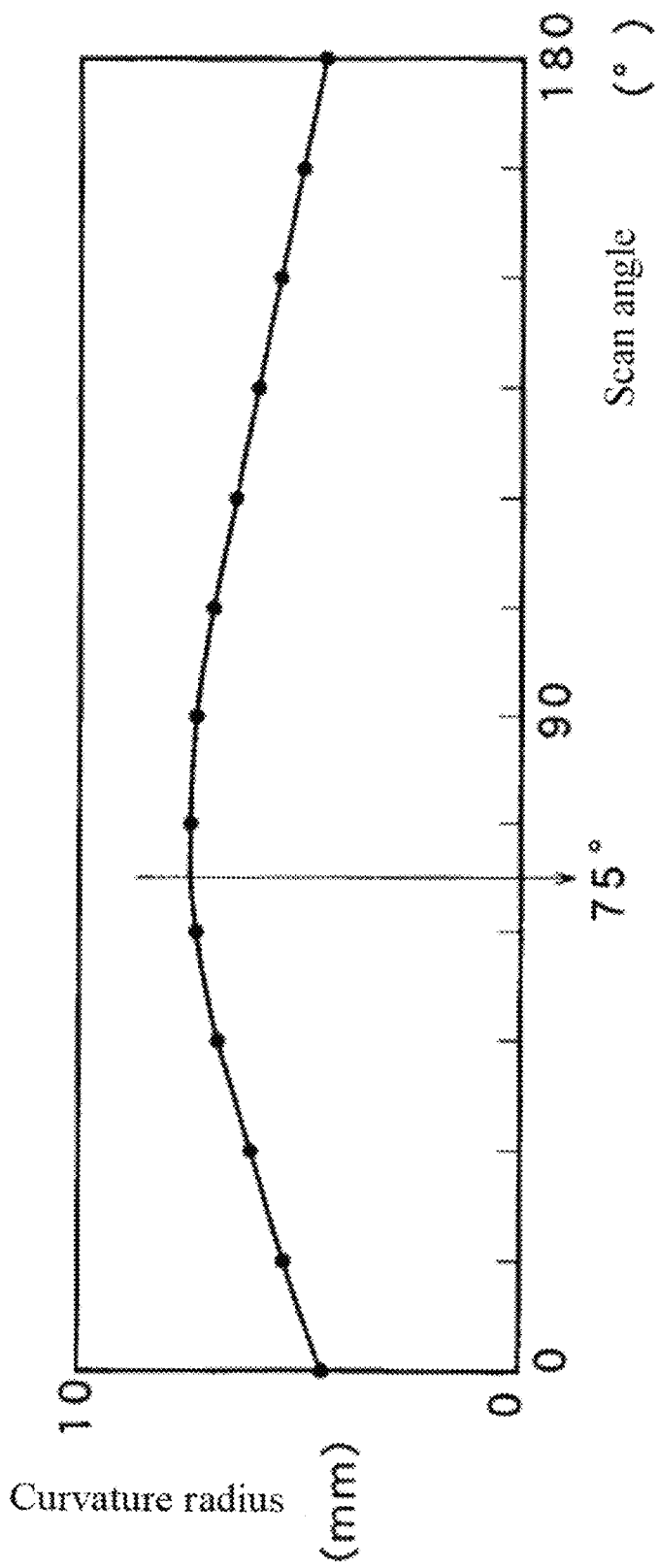
FIG. 19 is a diagram showing a graph that shows the change in curvature radius at an angle.

Further, when the person to have the measurement taken is astigmatic, the curvature radius of the cornea is different depending on the direction. Therefore, as shown in FIG. 18, the curvature radius of the cornea for every predetermined angle and a plurality of points, in the shape of a ring, are irradiated for every predetermined angle, for example, every 22.5 degrees, and the curvature radius of each direction is measured. According to the present embodiment, the x direction, and the y direction are scanned at the same focus. Therefore, parallel scanning is entirely enabled at in intermediate diagonal angle of the x-axis and the y-axis by combining the scanning in the x direction and the y direction. The radial scanning as shown in FIG. 18 is repeated, and the curvature radius is found with each section according to the calculation method described above. The curvature radius of each direction can be found when carried out in this manner. As shown in FIG. 19, this result is compiled in a graph, and the curvature radius is modified in accordance with the angle. When the angle to become the maximum of the curvature radius is found from this graph by interpolation, the angle becomes the astigmatic axis. For example, an angle of approximately 75° becomes the astigmatic axis in the case of FIG. 19.

Arithmetic Processing for the Degree of Cloudiness

Figure 20:
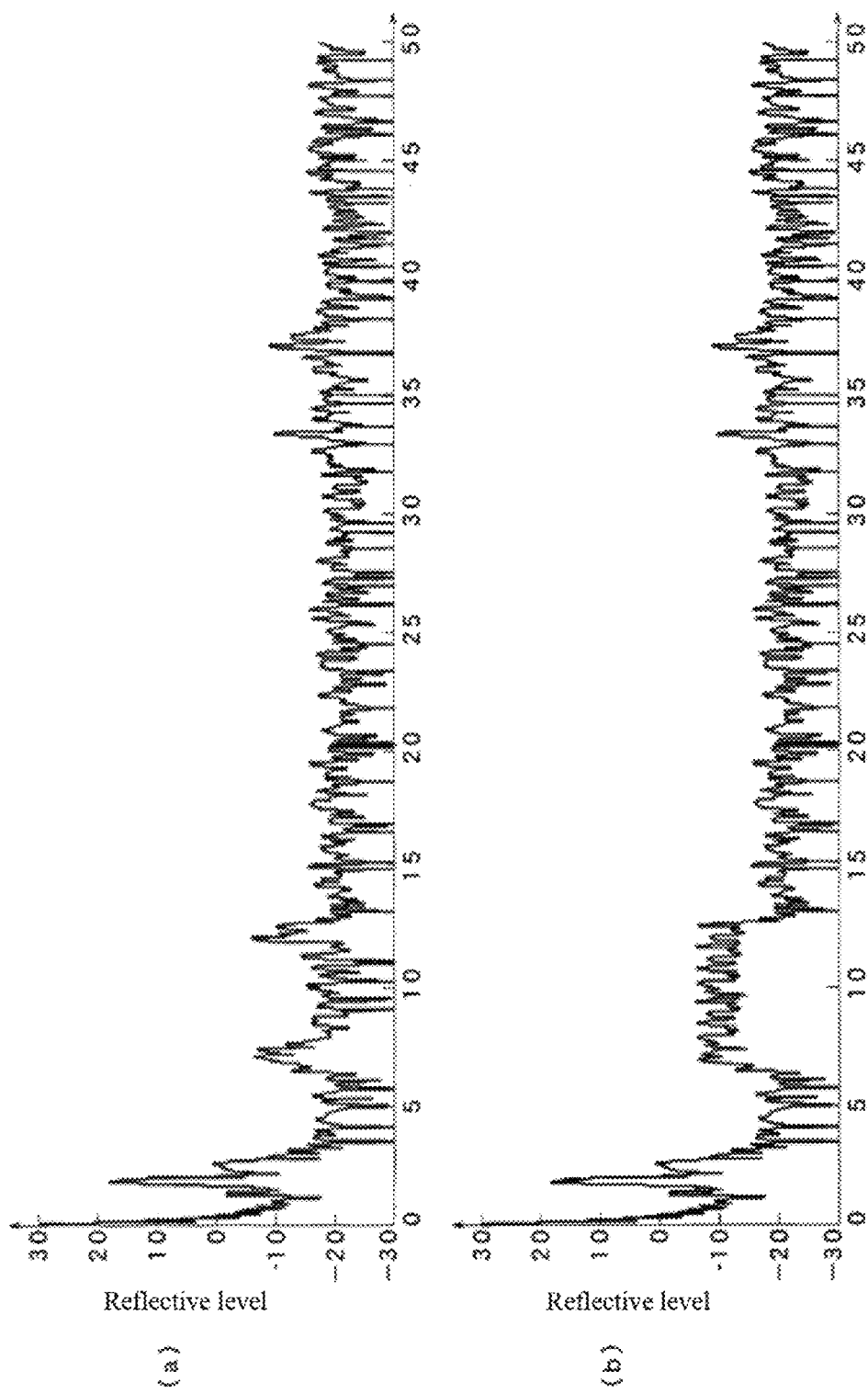
FIG. 20 is a graph showing a change in a reflective level at the central part of a cross-sectional image.

Next, the arithmetic processing for the degree of cloudiness of the lens in the routine R26 will be described. In the signal processing, when the lens (the crystalline lens) is cloudy, the reflectance of the lens back side decreases and the signal strength of the center increases due to the scattering. FIG. 20($a$) shows a normal unclouded condition, and FIG. 20($b$) shows the cloudiness condition worsening. Therefore, the degree of cloudiness is numerically evaluated based on the difference between the surface of the lens and the reflection level of the back side or the difference between the reflection level of the lens inside and the center, or both of these level differences, and the indexed degree of cloudiness is displayed. For example, assuming the average brightness of the predetermined range of the surface of the vicinity of the center is P(×1), and the average brightness of the predetermined range of the back side of the vicinity of the center is P(×2), then a coefficient is multiplied by P(×1)−P(×2) or by P(×1)/P(×2) to find the degree of cloudiness. This can be used as the standard for determining whether an operation is needed for the degree of cloudiness.

Next, the ophthalmic optical tomographic image display device is described according to the second embodiment of the present invention. In this embodiment, the interferometer comprises a space interferometer, and has a switching function to change the measurement range of the z-axis direction on the spot. When considering that the ocular axial length of the person is roughly the range of around 15-30 mm, and the refractive index of the vitreous body inside the eyeball is about 1.37, the measurement range that is found in the measurement of the ocular axial length becomes 20-40 mm as the optical path. Therefore, a coherence length of 20-40 mm is found as the coherence length of the light source. A maximum coherence length of around 30-40 mm can be obtained by performing the wavelength scanning at high speed; however, the level of the OCT signal at the longest edge decrements 6-10 dB in comparison with the level of 0 point.

In addition, since there is also a decrement of the absorption of the infrared light by the vitreous body or the signal due to the scattering of light by the cloudiness of the cataract, it is preferable to make the coherence length as long as possible. However, it is difficult to balance the high coherence length with high-speed scanning. Normally, the interference zero point is set on this side of the sample surface, and the side where the light path length of the sample side extends from the point is imaged as the imaging range of the positive side. Contrary to this, in this embodiment, the zero point at 50 mm inside from the surface of sample with a sufficient margin is set for the rear of the retina, for example, the ocular axial length, and the imaging range is reversed. When carried out in this manner, the influence of the decrementing due to the coherence length of the light source can be suppressed on the retina side, where light is hardest to reach, and the measurement success rate of the ocular axial length can be improved even in the case of a severely clouded cataract.

Figure 21:
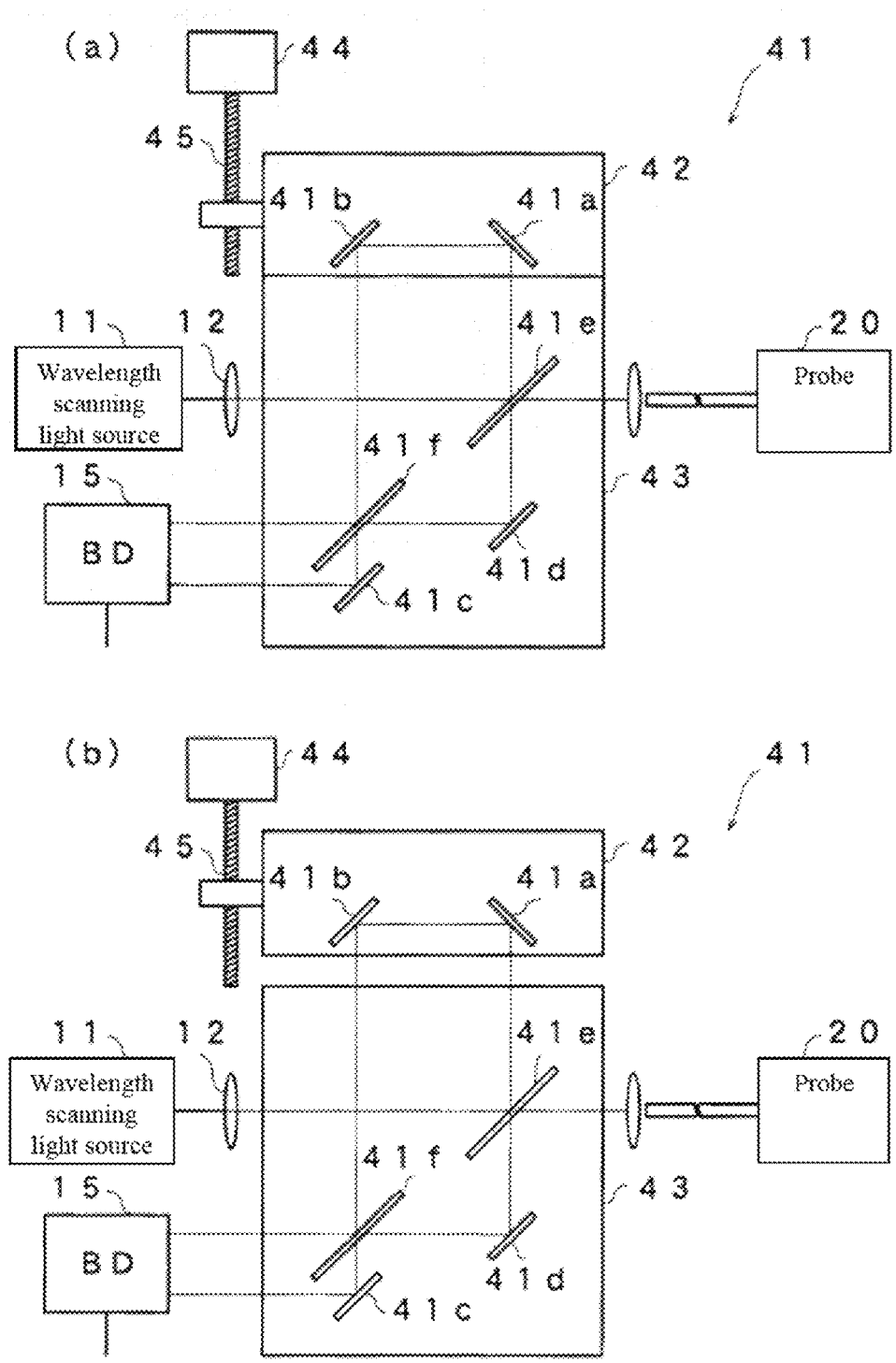
FIG. 21 is a diagram showing the main part of a consultation optical meter of the probe portion of an optical tomographic image display device according to the second embodiment of the present invention.

Therefore, in this embodiment, a mechanism is provided to switch the imaging of this negative side, and the light path length in the light path of the interferometer side or the sample side to, for example, around 50 mm, and it is configured to switch at high speed at the time of a single measurement. An interferometer 41 of this embodiment is the same as that of the first embodiment described in FIG. 21, and it uses mirrors 41$a$ and 41$d$, and half mirrors 41$e$ and 41$f$. Components other than the interferometer 41 are similar to those of the first embodiment. Therefore, detailed descriptions will be omitted. Then, the interferometer 41 is configured to be able to separate a moving part 42, which holds the mirrors 41$a$ and 41$b$, from a fixed part 43 having the other optical components. As shown in FIG. 21, a motor 44 turning around the light path and a forwarding screw 45 rotating with this are used, and the moving part 42 is connected to the forwarding screw 45. When carried out in this manner, the moving part 42 can be moved by rotating the motor 44. The mirrors 41$a$ and 41$b$ of the moving part 42 can switch to a first state as shown in FIG. 21($a$) at the same position as in FIG. 1 and to a second state moving upward as shown in FIG. 21($b$). The light path difference of the reference light in these two states is set to 50 mm. The first state as shown in FIG. 21($a$) is a state with a zero point position in the vicinity of the surface of the eyeball, similar to the first embodiment. Meanwhile, in the second state of FIG. 21($b$), the fundus oculi part becomes the position of the zero point. When carried out in this manner, in the second state, an image of the vicinity of the fundus oculi can be displayed more definitely, and the ocular axial length can be measured precisely. However, the signal around the cornea uses the image data of the positive side when extracting the cornea shape, in other words, the curvature and lens thickness/thickens because the positive side is stronger.

Figure 22:
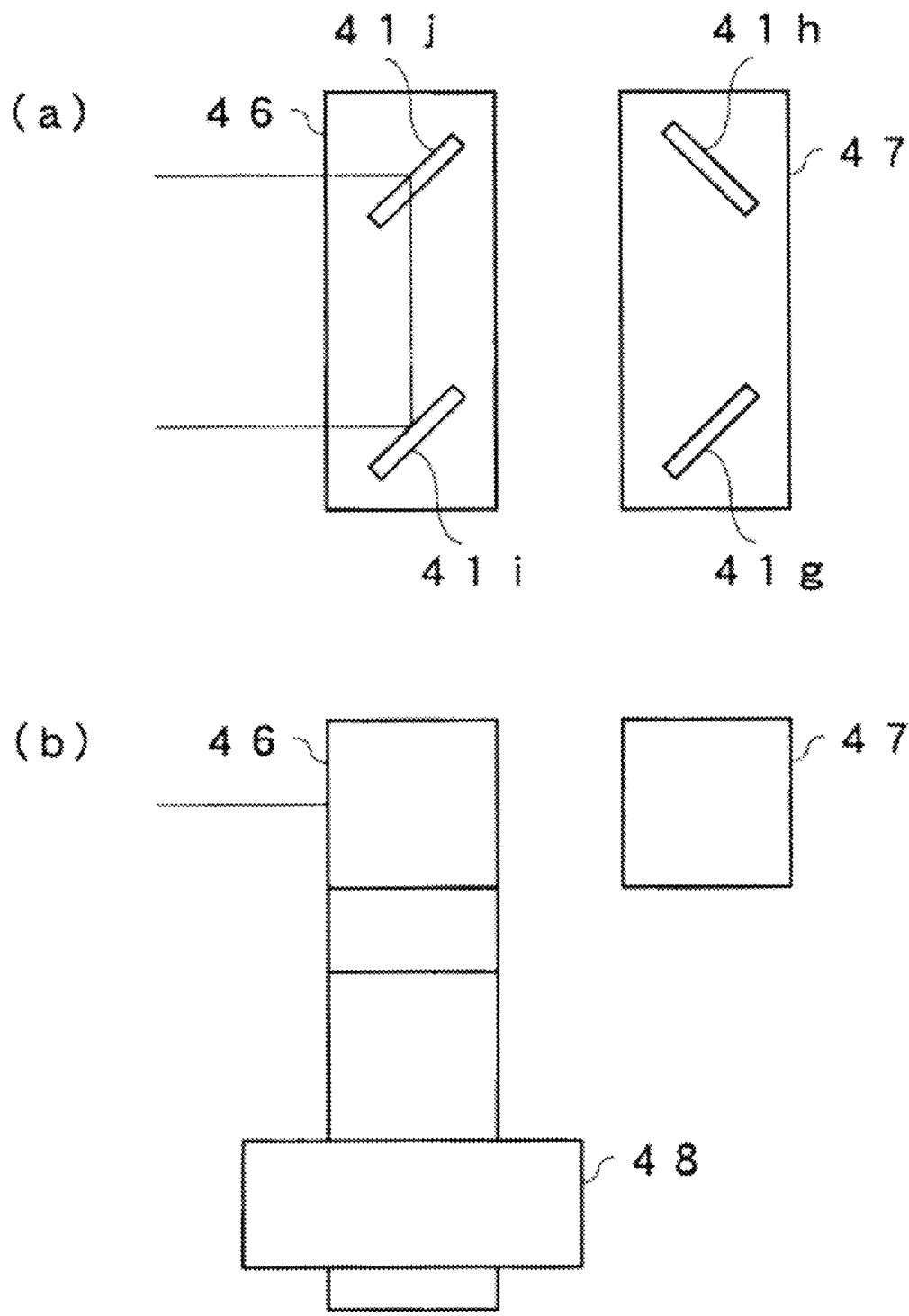
FIG. 22 is a diagram showing the main part of an interferometer according to a modification of the second embodiment of the present invention.
Figure 23:
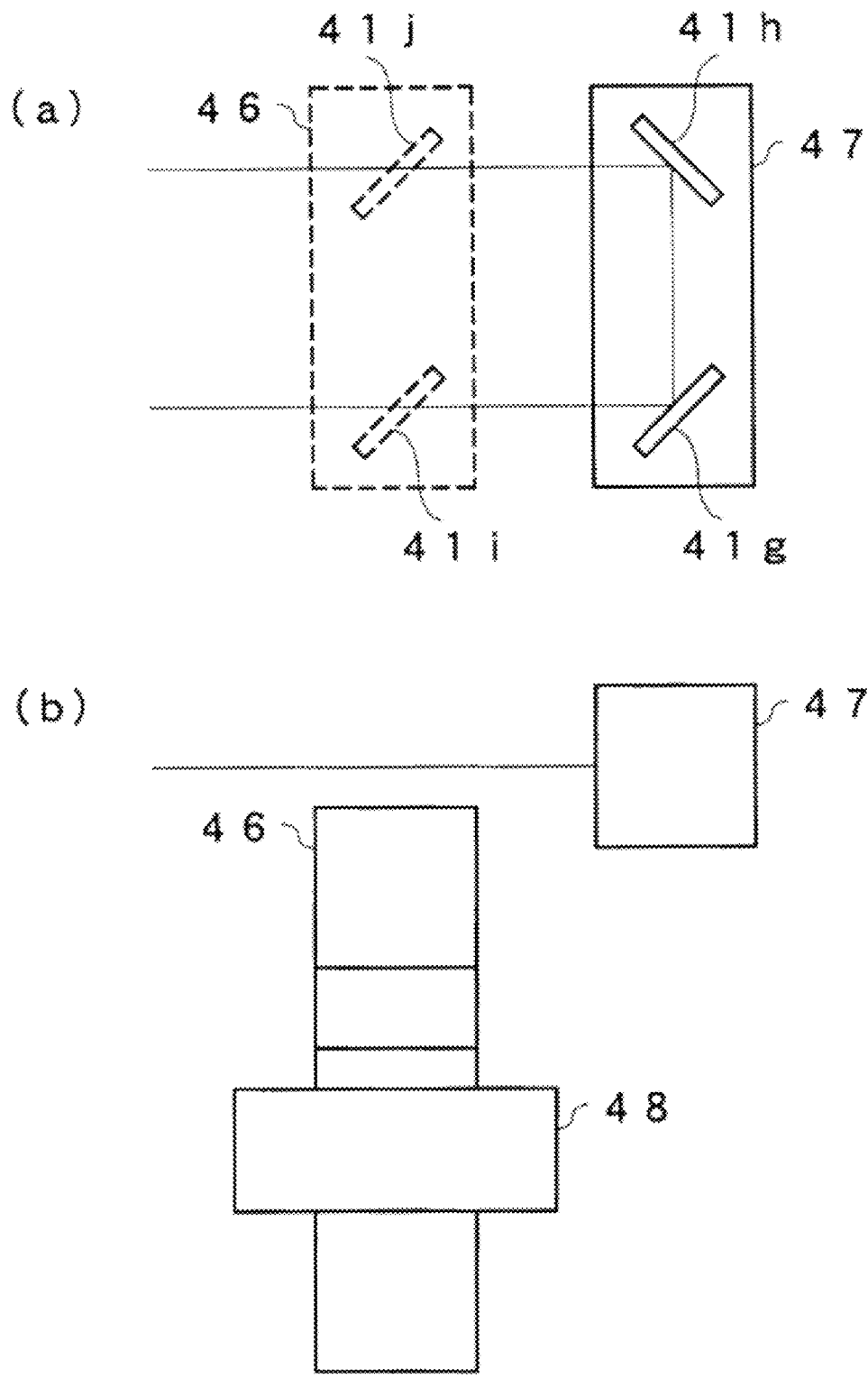
FIG. 23 is a diagram showing the main part of an interferometer according to a modification of the second embodiment of the present invention.

A modification example to change the light path length of the reference optical system of the interferometer at high speed will be described using FIG. 22 and FIG. 23. This method uses a moving part 46 and a fixed part 47 instead of the moving part 42, with the other configurations being similar to the above described embodiment. In this modification example, as shown in FIG. 22, the fixed part 47 holds mirrors 41g, 41h equivalent to the mirrors 41a, 41b. In addition, a moving part 46 holds mirrors 41i, 41j equivalent to these. As shown in FIG. 22 and FIG. 23, the moving part 46 is free to move in an up-and-down motion by a solenoid 48. Then, as shown in FIGS. 22(a) and (b), in the first state, to shorten the light path length, the moving part 46 is projected to the top by the solenoid 48, and the light is reflected by the mirrors 41g and 41h of the moving part 46. Meanwhile, when the light path length is made longer, the moving part 46 is pushed downward by solenoid 48. When carried out in this manner, the reference light is reflected by the mirrors 41i and 41j of the fixed part 47, and the light path length of the reference light can be made longer. Here, if the light path length difference before and after switching these is set at around 50 mm, then an ocular axial length can be kept in the imaging range by all means.

Figure 25:
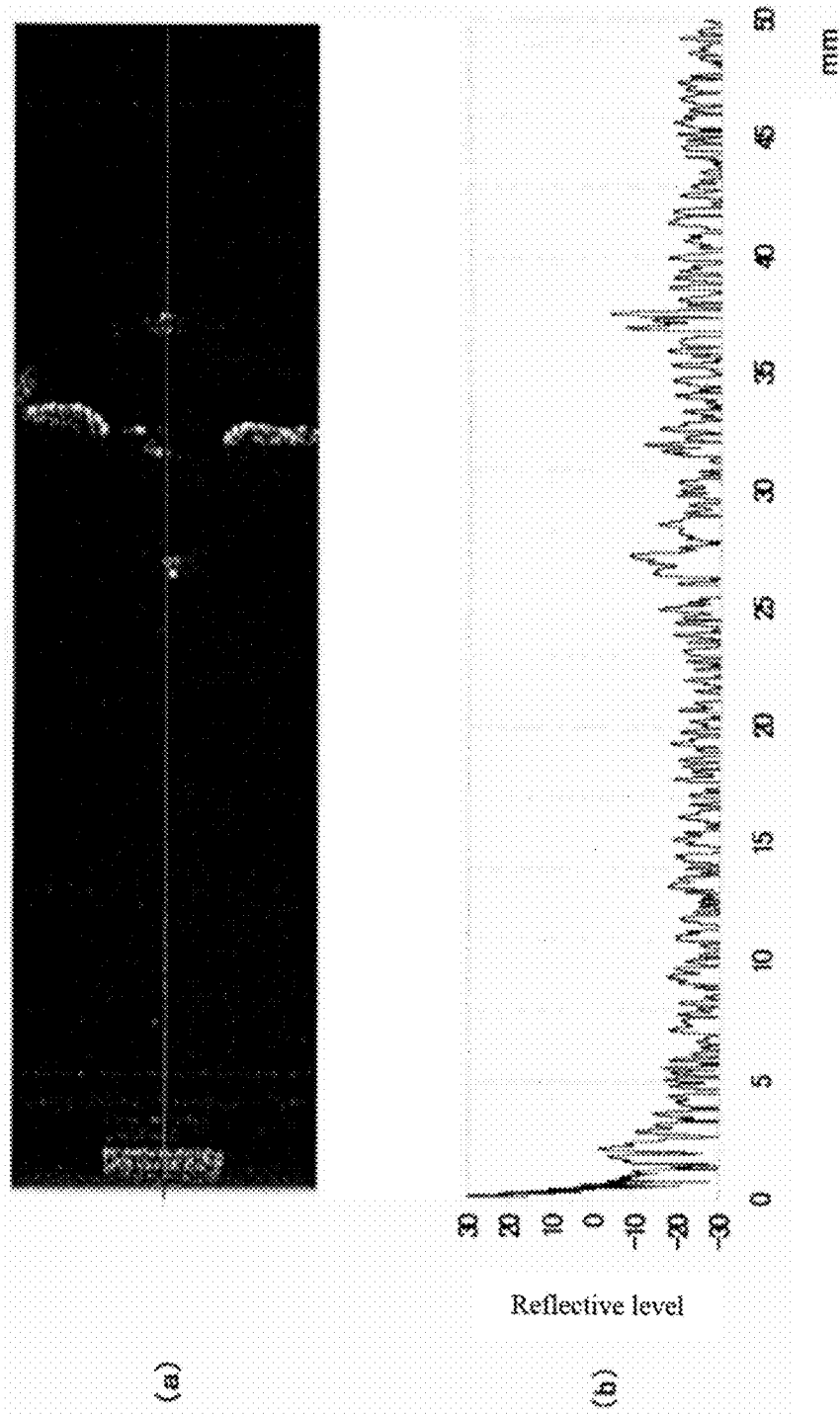
FIG. 25 is a graph showing a change in a reflective level at the center and the cross-sectional image in the second position according to the second embodiment of the present invention.

FIG. 24(a) is an example of an image when the sample is used as the zero point, which is similar to the first embodiment, with the moving part 42 as the first position, and FIG. 24(b) shows the output level on the centerline. FIG. 25(a) shows an example of an actual cross-sectional image when 50 mm zero point side is used as the inner part of the sample, with the moving part 42 as the second position, and FIG. 25(b) shows the output level on the centerline. In this way, the output of the cornea surface is large at the first position, and the brightness level lowers in the vicinity of the inner retina. Contrary to this, the output of the cornea surface is low at the second position; however, the retina and the inside image can be displayed more definitely since the vicinity of the inner retina is at a high-level.

Figure 27:
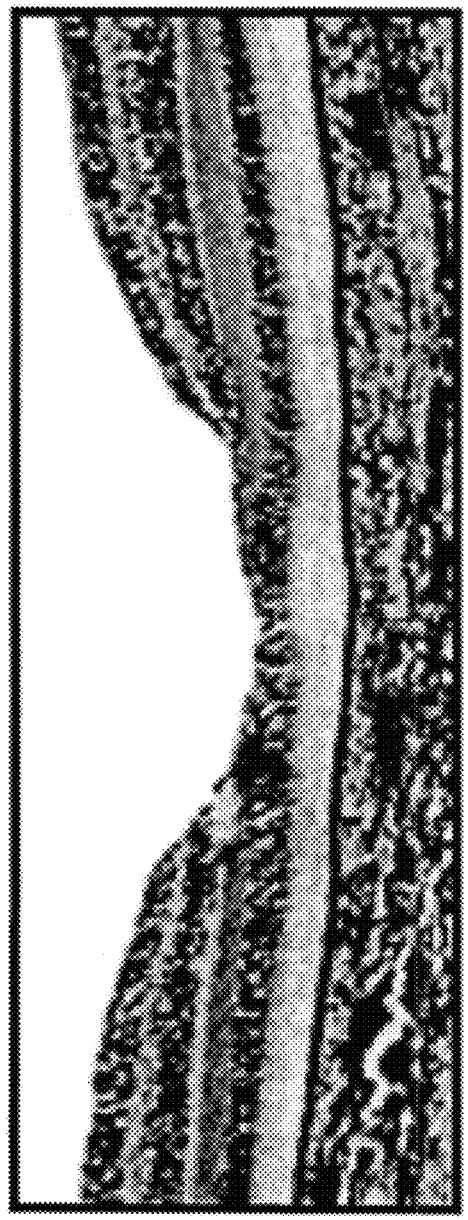
FIG. 27 is a diagram showing an example of a cross-sectional image in the second state according to the third embodiment of the present invention.

Next, the third embodiment of the present invention is described. The cross-sectional image display unit of this embodiment has a function to change to the tomographic observation mode of the retina. In this embodiment, the object lens 23 in FIG. 1 is made to freely detach, and when the object lens 23 is removed, the light of the two-axis tilt mirror 22a can be output directly to the object to be measured. The other configurations are similar to the first embodiment. FIG. 26(a) shows when the object lens 23 is attached, that is to say, it shows a measurement similar to the first embodiment, and if there is an object lens 23, the light only hits the center axis. Therefore, the tomographic image of the retina is not obtained. Next, freely detachable attached object lens 23 is removed, and the two-axis tilt mirror 22 is near to a distance from the cornea of about the ocular axial length La. When carried out in this manner, as shown in FIG. 26(b), scanning can be switched to a fan-shaped scanning about the tilt mirror 22 because there is no object lens 23. The light from the two-axis tilt mirror 22 will focus in the vicinity of the retina due to a lens in the eyeball which is the object to be measured. When carried out in this manner, the tomographic image of the retina can be detected by the tomographic image display device since the beam is almost scanned parallel on the retina (fundus oculi). FIG. 27 is an example of a tomographic image of a retina that obtained in this way. The structure of the retina can be observed based on such an image, and it can be used in the diagnosis of the illness of the retina for detached retinas, glaucoma, age-related macular degeneration, or the like.

Next, the fourth embodiment of the present invention will be described. In this embodiment, as shown in FIG. 28(a), the probe 20 is freely switched from an upright state, as shown by the solid line, and a state in which it turns 90°, as shown by the dashed line. In this embodiment, a joint mechanism to enable flexure so that the probe 20 is located on the side of the main body is provided when the beam is irradiated horizontally on the human eye seated on the probe 20 to be scanned with a light beam. As shown in FIG. 28(b), in the measurement before a surgical operation, the probe 20 is made to stand straight to correspond to the human body and positioned to measure the ocular axial length. In the surgical operation mode, as shown with the dashed line in FIG. 28(a) and in the side view of FIG. 28(c), the probe 20 is flexed 90°, and the beam is irradiated perpendicularly on the human eye laid on the treatment platform. When a measurement can be taken in such a position, the ocular axial length or the like can be reconfirmed just before an operation, and on the other hand, it can be used for operations on the vitreous body while watching the structure of the eyeball or as a guide for cataract surgery.

The present invention can detect an optical tomographic image for ophthalmology by eliminating the distortion of the optical axis direction and is useful as an image display device for ophthalmology because measurement data for operations of the cataract and the like can be acquired in a short time.

CONCLUSION

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations.

However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. An ophthalmic optical tomographic imaging device, comprising:
    a tunable light source to provide a wavelength-scanned beam;
    an interferometer, in optical communication with the tunable light source, to split the wavelength-scanned beam into a reference beam and an object beam;
    a collimator, in optical communication with the interferometer, to collimate the object beam;
    a probe, in optical communication with the collimator, to scan the object beam in a first dimension perpendicular to an optical axis of an eye and in a second dimension perpendicular to the optical axis of an eye, the probe comprising:
        an objective lens, in optical communication with the collimator, to focus the object beam to a spot within the eye; and
        a two-axis tilt mirror, disposed in a back focal plane of the objective lens, to tilt the object beam from the collimator so as to scan the spot along at least one of the first dimension and the second dimension; and
    a detector, in optical communication with the eye, to detect a beat signal caused by interference between the reference beam and at least a portion of the object beam reflected from the eye; and
    an image signal processing unit, operably coupled to the detector, to generate at least one tomographic image of at least a portion of the eye based on the beat signal.

2. The ophthalmic optical tomographic imaging device of claim 1, wherein the tunable light source is configured to scan a wavelength of the wavelength-scanned beam at a scanning speed of at least about 1 kHz.

3. The ophthalmic optical tomographic imaging device of claim 1, wherein the tunable light source is configured to scan a wavelength of the wavelength-scanned beam within a range of about 700 nm to about 1200 nm.

4. The ophthalmic optical tomographic imaging device of claim 1, wherein the tunable light source is configured to scan a wavelength of the wavelength-scanned beam by at least about 1 nm.

5. The ophthalmic optical tomographic imaging device of claim 1, wherein the interferometer comprises at least one adjustable mirror to change an optical path length of the reference beam so as to generate another beat signal representative of another portion of the eye.

6. The ophthalmic optical tomographic imaging device of claim 1, wherein the probe further comprises a flexure-free housing.

7. The ophthalmic optical tomographic imaging device of claim 1, wherein the objective lens is configured to be detached from the probe.

8. The ophthalmic optical tomographic imaging device of claim 1, wherein the image signal processing unit is configured to determine at least one of an ocular axial length, a corneal thickness, an anterior chamber thickness, a lens thickness, a retina thickness, a corneal diameter, a pupil diameter, and a cornea curvature radius based on the beat signal.

9. The ophthalmic optical tomographic imaging device of claim 1, wherein the image signal processing unit is configured to determine a location of at least one of the cornea, the crystalline lens, and an edge of the retina based on at least one of a maximum signal strength and an average signal strength within a predetermined portion of the at least one tomographic image.

10. The ophthalmic optical tomographic imaging device of claim 1, wherein the image signal processing unit is configured to estimate a radius of curvature of the cornea based on at least three points of a surface trace of the cornea.

11. The ophthalmic optical tomographic imaging device of claim 10, wherein the at least three points comprise three arbitrary points within a range of about 2 mm to about 3 mm on the surface trace of the cornea.

12. The ophthalmic optical tomographic imaging device of claim 1, wherein the image signal processing unit is configured to estimate a degree of cloudiness of the crystalline lens based on a reflectance measurement of a front of the crystalline lens and a reflectance measurement of a back of the crystalline lens.

13. The ophthalmic optical tomographic imaging device of claim 1, further comprising:
    a scan control unit, operably coupled to the two-axis tilt mirror, to change a center of a scan range in at least one of the first dimension and the second dimension.

14. A method of ophthalmic optical tomographic imaging, the method comprising:

(A) generating a wavelength-scanned beam;
(B) splitting the wavelength-scanned beam into a reference beam and an object beam;
(C) collimating the object beam;
(D) focusing the object beam to a spot within the eye using an objective lens;
(E) tilting the object beam with a two-axis tilt mirror disposed in a back focal plane of the objective lens so as to scan the spot along at least one of a first dimension and a second dimension perpendicular to the optical axis of the eye;
(F) detecting a beat signal caused by interference between the reference beam and at least a portion of the object beam reflected from the eye; and
(G) generating at least one tomographic image of the eye based on the beat signal.

15. The method of claim 14, wherein (A) comprises scanning a wavelength of the wavelength-scanned beam at a scanning speed of at least about 1 kHz.

16. The method of claim 14, wherein (A) comprises scanning a wavelength of the wavelength-scanned beam within a range of about 700 nm to about 1200 nm.

17. The method of claim 14, wherein (A) comprises scanning a wavelength of the wavelength-scanned beam by at least about 1 nm.

18. The method of claim 14, wherein (E) comprises changing a scan range of the spot in at least one of the first dimension and the second dimension.

19. The method of claim 14, further comprising:
(H) changing an optical path length of the reference beam so as to produce another beat signal representative of another portion of the eye.

20. The method of claim 14, further comprising:
(I) determining at least one of an ocular axial length, a corneal thickness, an anterior chamber thickness, a lens thickness, a retina thickness, a corneal diameter, a pupil diameter, and a cornea curvature radius based on the beat signal.

21. The method of claim 14, further comprising:
(J) determining a location of at least one of the cornea, the crystalline lens, and an edge of the retina based on at least one of a maximum signal strength and an average signal strength within a predetermined portion of the at least one tomographic image.

22. The method of claim 14, further comprising:
(K) estimating a radius of curvature of the cornea based on at least three points of a surface trace of the cornea.

23. The method of claim 22, wherein (K) further comprises selecting three arbitrary points within a range of about 2 mm to about 3 mm on the surface trace of the cornea.

24. The method of claim 14, further comprising:
(L) estimating a degree of cloudiness of the crystalline lens based on a reflectance measurement of the front of the crystalline lens and a reflectance measurement of the back of the crystalline lens.

25. An ophthalmic measurement device, comprising:
a tunable light source to provide a wavelength-scanned beam;
an interferometer, in optical communication with the tunable light source, to split the wavelength-scanned beam into a reference beam and an object beam;
a collimator, in optical communication with the interferometer, to collimate the object beam;
a probe, in optical communication with the collimator, wherein the probe is configured to scan the object beam at a constant speed, the probe comprising:
a two-axis tilt mirror, in optical communication with the collimator, to tilt the object beam with respect to an optical axis of an eye; and
an objective lens, disposed an optical distance f from the two-axis tilt mirror, to focus the object beam to a spot within the eye so as to scatter light from at least one structure in the eye;
a detector, in optical communication with the eye, to detect a beat signal caused by interference between the reference beam and at least the light scattered from the eye; and
a signal processing unit, operably coupled to the detector, to determine at least one of an ocular axial length, a corneal thickness, an anterior chamber thickness, a lens thickness, a retina thickness, a corneal diameter, a pupil diameter, and a cornea curvature radius based on the beat signal.

26. A method of ophthalmic measurement, the method comprising:
(A) generating a wavelength-scanned beam;
(B) splitting the wavelength-scanned beam into a reference beam and an object beam;
(C) collimating the object beam;
(D) tilting the object beam with respect to an optical axis of an eye with a two-axis tilt mirror so as to scan an object along at least one of a first dimension and a second dimension perpendicular to the first dimension;
(E) focusing the object beam to a spot within the eye using an objective lens having a focal length f and disposed an optical distance f from the two-axis tilt mirror;
(F) detecting a beat signal caused by interference between the reference beam and at least a portion of the object beam reflected from the eye;
(G) determining distortion over an imaging range of the object in at least one of the first dimension and the second dimension;
(H) compensating for the distortion in at least one of the first dimension and the second dimension; and
(I) determining at least one of an ocular axial length, a corneal thickness, an anterior chamber thickness, a lens thickness, a retina thickness, a corneal diameter, a pupil diameter, and a cornea curvature radius based on the beat signal.

* * * * *

UNITED STATES PATENT AND TRADEMARK OFFICE
CERTIFICATE OF CORRECTION

PATENT NO.        : 8,690,328 B1
APPLICATION NO.   : 13/892997
DATED             : April 8, 2014
INVENTOR(S)       : Changho Chong Page 1 of 1

It is certified that error appears in the above-identified patent and that said Letters Patent is hereby corrected as shown below:

IN THE CLAIMS

Claim 25, Column 18, Line 15 delete "f" and insert -- $f$ --

Claim 26, Column 18, Line 40 delete "lengthfand" and insert -- length $f$ and --

Claim 26, Column 18, Line 41 delete "f" and insert -- $f$ --

Signed and Sealed this
Twenty-ninth Day of July, 2014

Michelle K. Lee
*Deputy Director of the United States Patent and Trademark Office*